(12) United States Patent
Reed et al.

(10) Patent No.: US 10,617,553 B2
(45) Date of Patent: Apr. 14, 2020

(54) NECK ORTHOSIS

(71) Applicant: THE UNIVERSITY OF SHEFFIELD, Sheffield (GB)

(72) Inventors: Alexander Heathcliff Reed, Sheffield (GB); Joseph Langley, Sheffield (GB); Andrew Stanton, Sheffield (GB); Nicola Heron, Sheffield (GB); Christopher McDermott, Sheffield (GB)

(73) Assignee: THE UNIVERSITY OF SHEFFIELD, Sheffield (GB)

( * ) Notice: Subject to any disclaimer, the term of this patent is extended or adjusted under 35 U.S.C. 154(b) by 755 days.

(21) Appl. No.: 14/889,828

(22) PCT Filed: May 9, 2014

(86) PCT No.: PCT/GB2014/051432
§ 371 (c)(1),
(2) Date: Nov. 6, 2015

(87) PCT Pub. No.: WO2014/181128
PCT Pub. Date: Nov. 13, 2014

(65) Prior Publication Data
US 2016/0074202 A1    Mar. 17, 2016

(30) Foreign Application Priority Data
May 9, 2013 (GB) .................................. 1308366.2

(51) Int. Cl.
*A61F 5/055* (2006.01)

(52) U.S. Cl.
CPC .................................... *A61F 5/055* (2013.01)

(58) Field of Classification Search
CPC .. A61F 5/055; A61F 5/05883; A61F 5/05833; A61F 5/05816
USPC ............................................................ 602/18
See application file for complete search history.

(56) References Cited

U.S. PATENT DOCUMENTS

| | | | | |
|---|---|---|---|---|
| 2,818,063 A | * | 12/1957 | Smith | A61F 5/055 128/DIG. 23 |
| 3,189,026 A | | 6/1965 | Barnett | |
| 3,504,667 A | * | 4/1970 | McFarlane | A61F 5/055 602/18 |
| 3,717,143 A | * | 2/1973 | Johnson | A61F 5/028 602/19 |
| 4,325,363 A | * | 4/1982 | Berkeley | A61F 5/055 128/DIG. 23 |
| 5,366,438 A | | 11/1994 | Martin, Sr. | |
| 5,722,939 A | | 3/1998 | Hohlen | |

(Continued)

*Primary Examiner* — Tarla R Patel
(74) *Attorney, Agent, or Firm* — Maschoff Brennan

(57) ABSTRACT

A neck orthosis, head support system and method of use for supporting a head of a patient having a medical condition are described. The neck orthosis can comprise a body made of a material which is flexible and stretchy and a releasable fastener. The neck orthosis is shaped to cause the neck orthosis snuggly to conform to the anatomy of the patient adjacent the neck of the patient when the neck support is secured in use about the neck of the patient by the releasable fastener to support the head of the patient. A head support system can include a plurality of different support members which can be releasably attached to the neck orthosis to provide different types of support to the head of the patient.

29 Claims, 15 Drawing Sheets

(56) References Cited

U.S. PATENT DOCUMENTS

| | | | |
|---|---|---|---|
| 5,865,773 A * | 2/1999 | Koledin | A61F 5/055 |
| | | | 128/DIG. 23 |
| 5,904,662 A | 5/1999 | Myoga | |
| 6,464,658 B1 | 10/2002 | Darcey | |
| 7,743,736 B2 * | 6/2010 | Winestock | A01K 13/006 |
| | | | 119/814 |
| 7,785,359 B2 | 8/2010 | Latham | |
| 2003/0195444 A1 | 10/2003 | Gerstmar | |
| 2011/0184325 A1 * | 7/2011 | Behzadian | A61F 5/026 |
| | | | 602/19 |
| 2015/0112238 A1 * | 4/2015 | Cockerill | A61F 5/055 |
| | | | 602/18 |

* cited by examiner

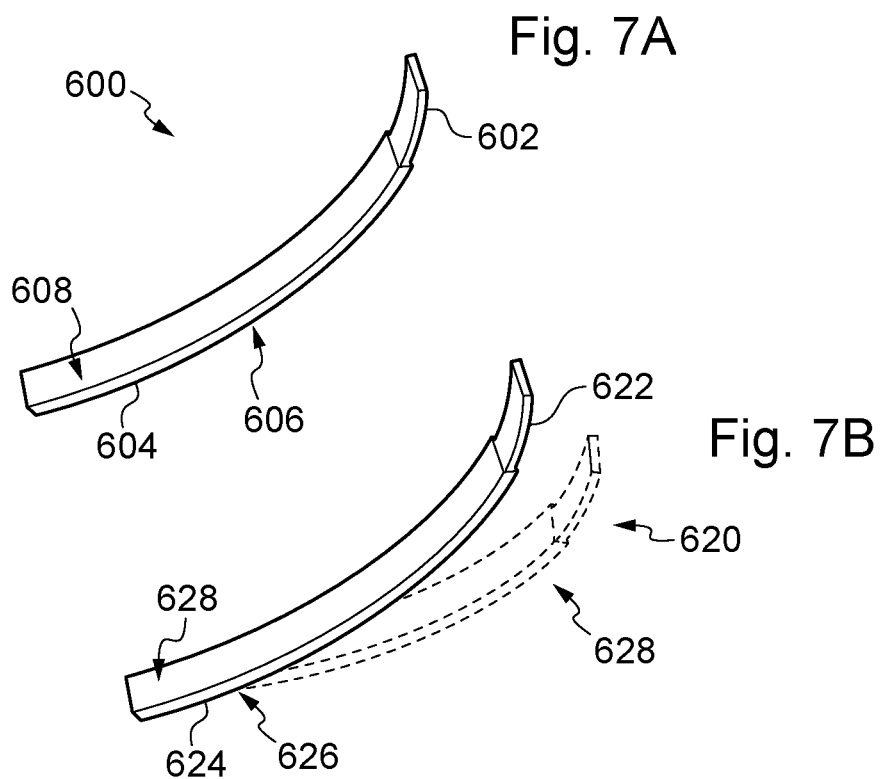
Fig. 7A
Fig. 7B
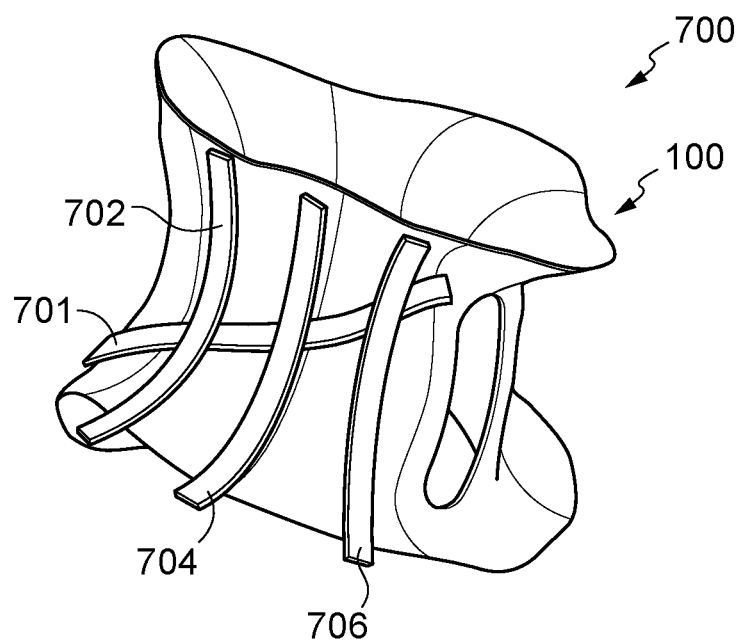
Fig. 8

NECK ORTHOSIS

The present invention relates to a medical orthosis and in particular a medical neck orthosis which can appropriately support the head of a patient suffering a medical condition and/or different stages of a medical condition.

Neck braces and collars are generally known. They are often used in traumatic head or neck injury to either immobilise the head and/or and also to deal with whiplash effect. Neck collars can also be are also used therapeutically to help realign the spinal cord and relieve pain. Neck collars can also be used for strains or sprains to the neck.

However, neck supports suitable for a specific medical condition, rather than injury are not common. The neck support requirements for different patients suffering a specific medical condition can be varied and can also depend on the particular stage of the medical condition. Neck supports for trauma and injury can have some degree of adaptability but are not tailored to address the specific symptoms arising from a particular condition nor to accommodate the wide range of patients and/or the wide range of stages or degrees of severity of the medical condition.

There is therefore a demand for a neck orthosis which can be used by patients suffering a particular medical condition, rather than a transitory injury. There is also a demand for a neck support which can accommodate a variety of stages or severity of a medical condition and/or for a wide variety of patients.

A first aspect of the invention provides a neck orthosis for supporting a head of a patient having a medical condition, comprising: a body made of a resilient, flexible material, the body having an outer surface, an inner surface, a top edge and a bottom edge; and a releasable fastener, wherein the neck support can be secured about a neck of the patient by the releasable fastener to support the head of the patient.

The top edge and the bottom edge can be shaped to cause the neck orthosis snuggly to conform to the anatomy of the patient adjacent the neck of the patient when the neck support is secured in use about the neck of the patient by the releasable fastener.

The material can be a four-way stretch material. This helps to make the neck orthosis move with the patient's head and/or neck while being worn by the patient.

The top edge and/or the bottom edge can follow a non-planar path. The path can follow a non-uniform curve.

The top edge can be stiffer than the material of the body of the neck orthosis. This reduces the amount of stretch in the material locally to the top edge.

The top edge can comprise a plurality of portions each adapted to match or conform to a different region part of the human anatomy above the neck. The top edge can comprise one or more of: a front portion shaped to receive an underside of a human lower jaw; a first side portion and/or a second side portion, each shaped to follow the mandible of a human; and a rear portion shaped to follow the lower cranium of a human.

The bottom edge can comprise a plurality of portions each adapted to match or conform to a different region part of the human anatomy below the neck. The bottom edge can comprise one or more of: a front portion shaped to project inferiorly over the clavicle toward the upper sternal region; a first side portion and/or a second side portion, each shaped to project laterally and across the trapezius of a human; and a rear portion shaped to project inferiorly and over the cervical vertebrae a human.

The body can have the form of a non-flat strip of the material.

The strip of material can have a length of between about 30 cm to about 50 cm, and preferably about 35 cm to 45 cm.

The strip of material can have a width of between about 20 cm to about 30 cm.

The strip of material can have a thickness of between about 2 mm to about 4 mm, preferably between about 2.5 mm and 3.5 mm and most preferably substantially 3 mm.

The material can be resiliently deformable, stretchy or elastic along its length and/or its width. Preferably, the material has an elastic modulus or Young's modulus (E) of from about 1.5 MPa to about 5 MPa, preferably at least about 2 MPa and most preferably about 2.4 MPa.

The material can be partially stiff, but still flexible.

Preferably, the material has an ultimate tensile strength, $\sigma_{UTS}$, of from about 6 MPa to about 11 MPa, preferably at least about 8 MPa, and most preferably about 8.4 MPa.

Preferably, the material has an elongation of from about 190% to about 230%, preferably at least about 210% and most preferably about 218%.

The body can be constructed from a plurality of panels. The individual panels can be flat and shaped to provide the overall three-dimensional configuration of the neck orthosis. Adjacent pairs of panels can be joined by flat seams. Each flat seam can be formed by panel edges butting together. Each seam can be formed by stitching, for example using a surgery seam or flat lock seam.

The body can be constructed from at least four, preferably at least six panels and more preferably eight panels or at least eight panels. The plurality of panels can include pairs of panels, the shapes of which are mirror images of each other.

The eight panels can include one or more of: one or a pair of front panels; one or a pair of forward side panels; one or a pair of rearward side panels; and one or a pair of rear panels. The shape of each panel of a pair of panels can be the same, but mirror images of each other.

The neck orthosis can include one or more pressure relief formations. A pressure relief formation can be provided at the front of the neck orthosis. The pressure relief formation can be positioned or otherwise arranged to cover the larynx of a human or the patient in use.

The pressure relief formation can comprise an elongate aperture in the material. The pressure relief formation can further comprise a support structure extending at least partially, or preferably entirely, around the periphery of the aperture.

The pressure relief formation can comprises an elongate section of a further material different to the material of which the body is made.

The material of the body can be breathable. The body can include a plurality of apertures to allow the egress of moisture.

The inner surface can comprise a wicking material which can transport moisture away from the skin of the patient.

The outer surface can comprise a loop material or a hook material of a hook and loop type fastening system.

A second aspect of the invention provides a head support system comprising: the neck orthosis of the first aspect of the invention, and any preferred features thereof, and a support member. The neck orthosis and support member can provide between them a releasable attachment mechanism whereby the support member can be releasably attached to the neck orthosis.

The head support system can further comprise a plurality of support members.

The or each support member can be releasably attachable to the outer surface of the neck orthosis.

The plurality of support members can be the same.

The plurality of support members can be different.

A first group of the plurality of support members can be the same as each other and/or a second group of the plurality of support members can be different to each other.

The plurality of support members can include a first support member configured to provide a first type of support and a second support member configured to provide a second type of support. The first type of support can be different to the second type of support. The first and second type of support can be in different directions and/or of different strength.

The or each support member can be releasably attachable to the neck orthosis at a plurality of positions and/or orientations over the neck orthosis.

The plurality of positions and/or orientations can be continuous. Hence, the support provided by the neck orthosis and support member or members can be more precisely tailored to the individual requirement of each specific patient.

The or each support member can be releasably attachable to the neck orthosis at any position and/or orientation over the neck orthosis.

At least one or a plurality of support members can be rigid or static.

At least one or a plurality of support members can be resiliently deformable or flexible or dynamic.

The head support system can provide symmetric support or asymmetric support. The support can be symmetric or asymmetric in the medial-lateral and/or anterior-posterior and/or inferior-superior directions.

The releasable attachment mechanism can be a hook and loop type system.

The or each support member can comprise a core and a covering including at least a portion or an area of a hook material and/or a loop material. An entire face of the support member can be covered by the hook or loop material.

The medical condition can be neurological. The medical condition can be neurodegenerative diseases causing neck muscle weakness, such as motor neurone disease, Multiple Sclerosis, muscular dystrophies and other disorders in which neck weakness can occur, e.g. stroke, dystonia.

A third aspect of the invention provides an assembly of the head support system of the second aspect of the invention and any preferred features thereof.

A fourth aspect of the invention provides a head support system for supporting a head of a patient having a medical condition, comprising: a neck orthosis; and a plurality of support members, each support member having a different form configured to provide a different type of support. The neck orthosis and plurality of support members can provide between them a releasable attachment mechanism by which each of the support members can be releasably attached to the neck orthosis to provide a different type of support.

The neck orthosis can have an outer surface and the releasable attachment mechanism can allow each of the support members to be releasably attached to the outer surface of the neck orthosis at a plurality of positions and the plurality of positions can be continuous. Hence, the support provided by the neck orthosis and support members can be more precisely tailored to the individual requirement of each specific patient.

The plurality of positions can extend over at least a part of a first side of the neck orthosis and/or at least a part of a second side of the neck orthosis and/or at least a part of a front of the neck orthosis and/or at least a part of a rear of the neck orthosis.

The plurality of positions can extend over at least 25% of the area of the outer surface of the neck orthosis, at least 50% of the area of the outer surface of the neck orthosis, at least 75% of the area of the outer surface of the neck orthosis or at least 90% of the outer surface of the neck orthosis.

The plurality of positions extend over substantially the entirety of the area of the outer surface of the neck orthosis.

The plurality of support members can include a first type of support member which has a flat elongate shape. The first type of support member can be in the form of a slat, thin bar or beam.

The plurality of support members can include a second type of support member which is shaped to provide lateral support. The second type of support member can be curved along a longitudinal axis and/or curved along a transverse axis. The second type of support member can be a shoulder engaging support member. Two of the second type of support member can be provided.

The plurality of support members includes a third type of support member which is shaped to provide support in a superior direction.

The third type of support member can be a lower jaw or mandible support.

The third type of support member can be shaped to provide support in a posterior direction also.

The third type of support member can have a zig-zag shape or generally Z shape, and/or a mirror image thereof.

The third type of support member can have a central member, an upper member and a lower member. The upper member can be curved to accommodate a lower jaw or mandible of a patient in use. The lower member can be shaped to accommodate an upper chest of a patient in use. The central member can be arranged to be, or be, twisted in use.

The plurality of support members can include a fourth type of support member which resiliently biases the neck orthosis in a posterior direction.

The fourth type of support member can be, or can include, a leaf spring.

The leaf spring can transition from a curved state to a more linear state as the load applied to it increases.

The fourth type of support member can have a central member arranged to provide the resilient biasing. The fourth type of support member can include an upper member shaped to accommodate the rear of a patient's neck in use and/or a lower member shaped to accommodate an upper part of a patient's back in use.

The fourth type of support member can be generally J shaped, and/or a mirror image thereof.

The plurality of support members can include a fifth type of support member. The fifth type of support member can be configured or shaped to support a chin.

The fifth type of support member can be generally A shaped.

The fifth type of support member can include first and second side member and a first upper cross member extending between respective first ends of the first and second side members and a second lower cross member extending between the first and second side members. The upper cross member can be curved to accept a user's chin in use and/or the lower cross member can be curved to accept a user's neck in use.

The support members can include a disc shaped part at each free end or extremity of the parts of the support member.

At least one or a plurality of support members can be releasably attachable to the neck orthosis at a plurality of positions and/or orientations over the neck orthosis.

At least one or a plurality of support members can be releasably attachable to the neck orthosis at any position and/or orientation over the neck orthosis.

At least one or a plurality of support members can be rigid, or static.

At least one or a plurality of support members can be resiliently deformable, or dynamic.

The releasable attachment mechanism can be a hook and loop type system. Preferably the neck orthosis provides the loop part and the support members provide at least a hook part. The support members can provide a loop part and a hook part.

The or each support member can comprise a core and a covering including at least a portion of a hook material and/or a loop material.

At least one or a plurality of support members can comprise a covering including at least a portion of a hook material and at least a portion of a loop material.

The neck orthosis can further comprise padding or a padding element positioned at a front of the neck orthosis. The padding or padding element can be on or can provide an inner surface of the neck orthosis. The padding or padding element can define an aperture or recess within the padding element.

The periphery of the padding or padding element surrounding and defining the aperture or recess can include a plurality of slits or slots therein. These can allow the shape of the periphery of the aperture to deform to match the local anatomy of a user.

The padding or padding element can includes a first arm extending from a first side and/or a second arm extending from a second side and/or a tail extending downwardly.

The padding or padding element can be a foam material.

The medical condition can be neurodegenerative.

A fifth aspect of the invention provides an assembly of the head support system according to the fourth aspect of the invention and any preferred features thereof.

Preferred features of the neck orthosis can also be preferred features of the neck support system and vice versa.

A sixth aspect of the invention provides a method for supporting a head of a patient suffering a medical condition using a neck orthosis. The method can comprise wrapping a body made of a material which is flexible and stretchy about the neck of a patient suffering a medical condition and releasably fastening the body to cause the neck orthosis to conform snuggly to the anatomy of the patient adjacent the neck of the patient to support the head of the patient.

The method can further comprise releasably attaching a first support member to the neck orthosis to provide a first type of support to the head of the patient.

The method can further comprise releasably attaching a second support member to the neck orthosis to provide a second type of support to the head of the patient which is different to the first type of support.

The method can further comprise removing the first support member from the neck orthosis.

The method can further comprise attaching a first plurality of support members during a first stage of the condition. The method can further comprise attaching a second plurality of support members, different to the first plurality of support members during a second stage of the condition. The second plurality of support members can comprise different types of support members and/or a different arrangement of support members.

The second stage of the condition can be more or less severe than the first stage.

The condition can be neurodegenerative, such as motor neurone disease.

Embodiments of the invention will now be described in detail, by way of example only, and with reference to the accompanying drawings, in which:

FIG. 7A shows a perspective view of a first type of support member being part of a support system according to the invention;

FIG. 7B shows a perspective view of another first type of support member similar to that shown in FIG. 6A;

FIG. 8 shows a perspective view of an assembly of a support system according to the invention including a plurality of first type of support members;

Like items in the different Figures share common reference signs unless indicated otherwise.

Embodiments of the invention will be described with reference to a neck orthosis suitable for patients suffering from various stages of the example medical condition of motor neurone disease. However, it will be appreciated that the neck orthosis can be used for other long term medical conditions, particularly neurodegenerative diseases causing neck muscle weakness, such as motor neurone disease, Multiple Sclerosis, muscular dystrophies and other disorders in which neck weakness can occur, e.g. stroke, dystonia and similar.

Figure 1:
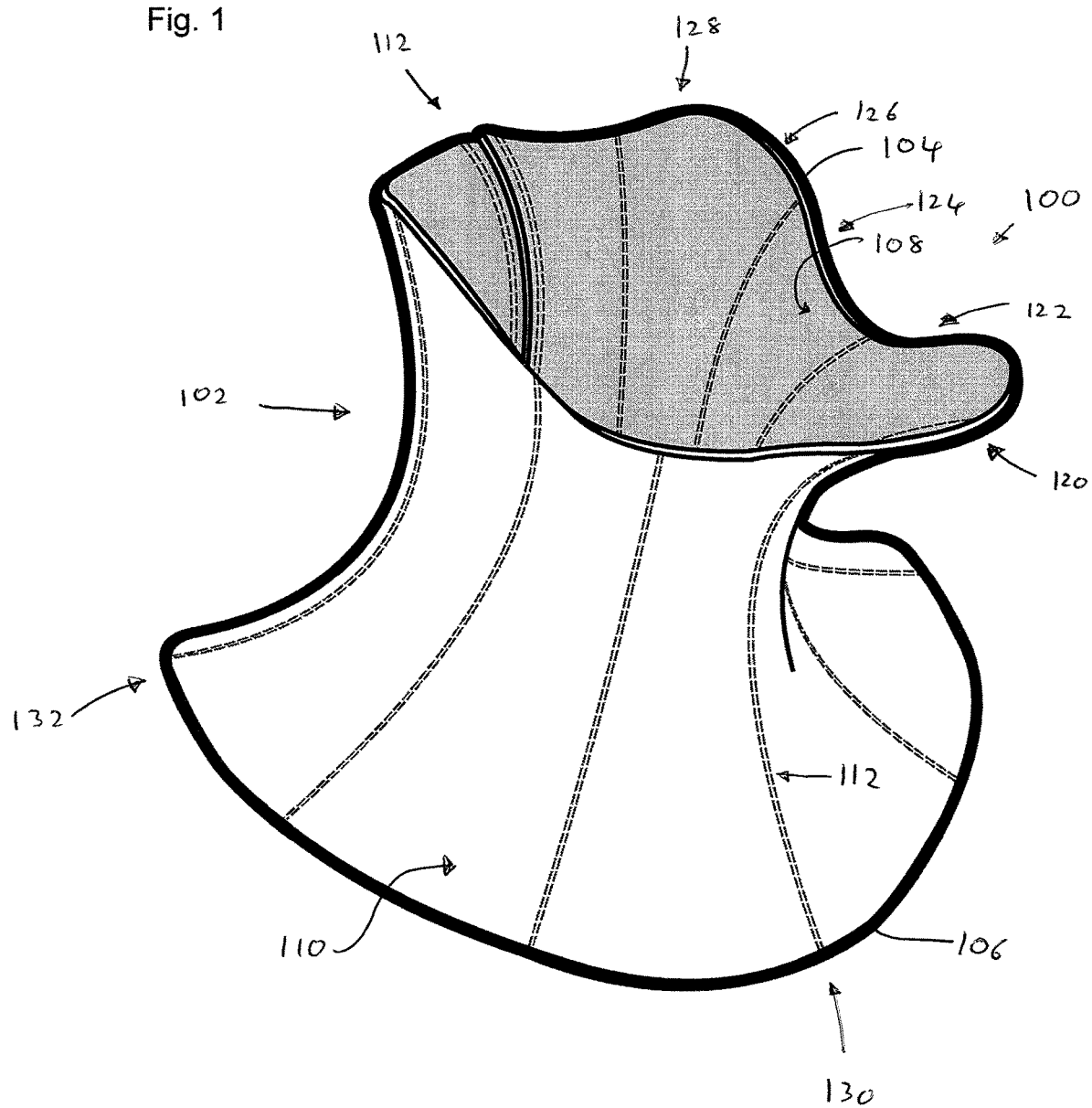
FIG. 1 shows a schematic perspective view of a first embodiment of a neck orthosis according to the invention.

With reference to FIG. 1, there is shown a perspective view of a first embodiment of a neck orthosis 100 according to the invention. FIG. 1 illustrates the ergonomic shape that the neck orthosis is arranged to adapt when secure in use about the neck of a patient to support the head of the patient. The neck orthosis generally has the form of a strip of flexible material but which is not flat as it is constructed to have the ergonomic shape illustrated in FIG. 1 so as to provide support to the head of a patent at an early or initial stage of a medical condition. The neck orthosis illustrated in FIG. 1 is particularly adapted to be used by patient's suffering from neurological conditions in which the muscles usually active to support the patient's head are not functioning normally.

The neck orthosis 100 has a body 102 with a top edge or profile 104, a bottom edge or profile 106, an inner surface 108 and an outer surface 110. The neck orthosis 100 also includes a releasable fastener (not visible in FIG. 1) toward the back or rear 112 which can be used to secure the neck orthosis about the neck of a patient in use. In alternative embodiments, the releasable fastener can be provided in other locations, such as toward the front or on either side of the neck orthosis so as to facilitate self-administration. The tope edge or profile 104 can include a stiffening component such as a flexible ribbon or cord of a material of sufficient strength to reduce the stretch of the material adjacent the top edge. The stiffening component can be made of a plastic such as Nylon, polyester or similar. An example is a 4 mm diameter braided polyester-acrylic cord.

Figure 2:
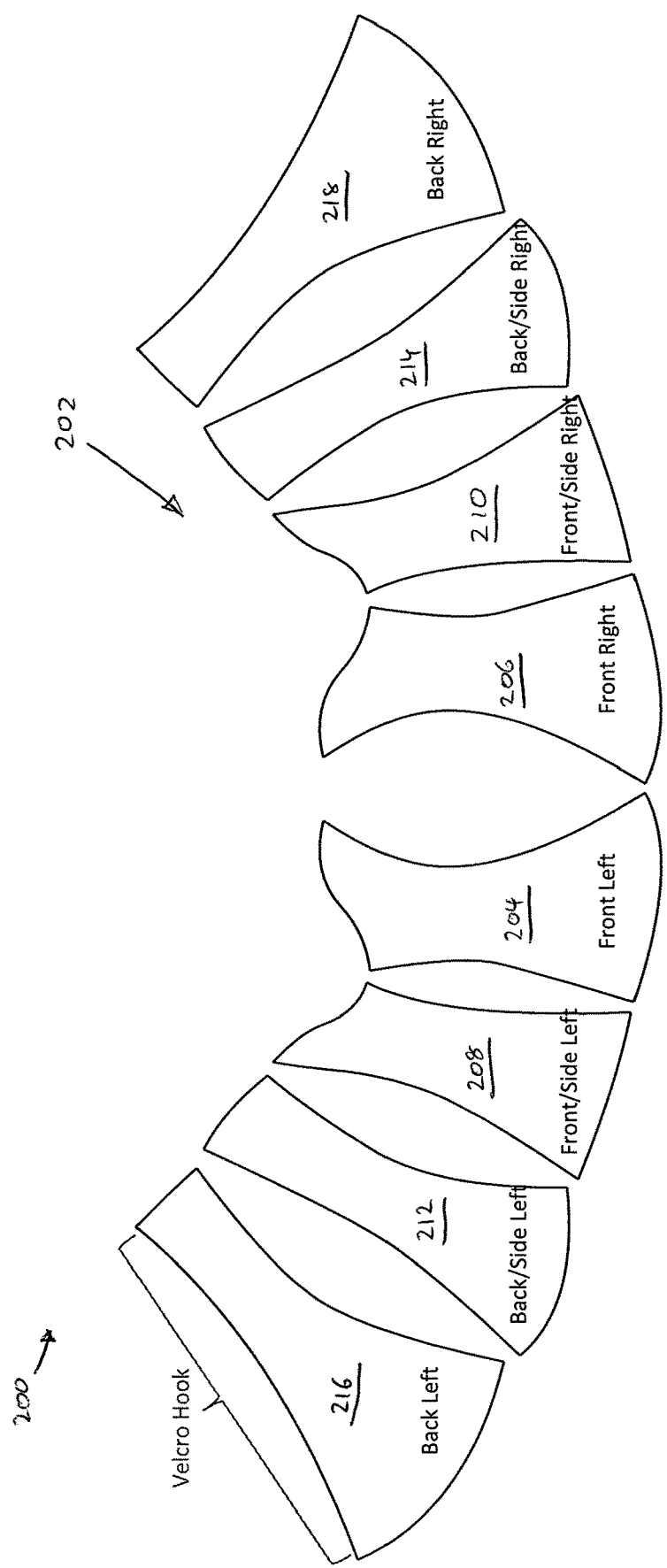
FIG. 2 shows a plan view illustrating the individual parts from which the neck orthosis is constructed.

The neck orthosis 100 is made from a plurality of individual panels. FIG. 2 shows a plan view of a cutting pattern 200 for the plurality of panels 202. The plurality of panels includes a pair of front panels 204, 206, a pair of forward side or lateral panels 208, 210, a pair of rearward side or lateral panels 212, 214, and a pair of rear panels 216, 218. The rear panels 216, 218 provide between them a releasable fastener mechanism as described in greater detail below. In particular, a one of them, e.g. 216, bears a hook material on a patient facing side which can be releasably attached to a loop material on an outward facing side of the other, e.g. 218. It will be appreciated that each panel of each pair of panels has generally the same shape but the panels are mirror images of each other. The plurality of panels 202 illustrated in FIG. 2 are sized and shaped to provide a neck orthosis suitable for use by an average medium sized man. It will be appreciated that the specific size and shape of the panels can vary depending on the specific details of the intended user, such as their age, size or gender. The panels shown in FIG. 2 are sized such that the length of the neck orthosis at a height corresponding to just below the level of the Adams apple is between about 35 cm to 45 cm. This encompasses the $5^{th}$ to $95^{th}$ percentiles for the male/female of 356.7 mm/329.4 mm to 441.1 mm/416.2 mm. The height of the orthosis can varying from about 20 cm at its narrowest to about 30 cm at its widest.

As best illustrated in FIG. 2, although the individual panels are themselves flat, they are cut so that when joined together they form the ergonomic, non-flat shape of the neck orthosis. Also, the top and bottom edges of the panels are cut so that they form continuous top 104 and bottom edges 106 respectively of the neck orthosis which describe respective paths or trajectories which engage the anatomy of the patient in specific locations so that the neck orthosis on its own can provide a level of support appropriate to an early stage of the medical condition. It will be noted that the respective paths described by the top and bottom edges do not follow a simple path such as an oval or ellipse or other simple cylinder (such as that defined by a simple foam neck brace) but rather vary in height and lateral position around the periphery in a non-uniform way so that local portions of the edge match the specific form of the local anatomy of the patient. It will also be noted that the shape of the top and bottom edges is not defined solely by the patient's anatomy (unlike, for example, a simple scarf), but rather are pre-formed by the construction of the neck orthosis. However, the neck orthosis can also deform or stretch to an extent to more closely match and snugly fit to an individual patient's specific anatomy.

The plurality of panels 202, and hence body 102, are made from a sheet of flexible material which is also resiliently deformable, i.e. elastic or stretchy, in at least four-directions ("four-way stretch"), i.e. along the body's longitudinal and width axes. However, the material is relatively thin, typically a few millimetres, and the body 102 has the shape of a non-flat strip of material when not in use.

The material of the body can also be engineered to transport perspiration, and allow the egress of other moisture away from the skin of the patient in use. A breathable material helps to ensure that the patient's skin remains dry and also enhances the thermo-regulatory effect providing improved comfort for the wearer. Breathability may be an inherent property of the material or the material may have a plurality of apertures introduced ranging from small 'pin pricks' up to larger apertures, to the extent that they do not significantly reduce the support behaviour of the neck orthosis.

In other embodiments, the inner surface 108 of the neck orthosis can also present a wicking material to help draw moisture away for the skin. The wicking can be an inherent property of the material of the body or an inner layer of wicking material separate to the flexible resilient material can be provided.

The outer surface 110 presents a looped material providing the loop part of a hook-and-loop releasable fastening system. The looped material extends over the entirety of the outer surface 110 of the neck orthosis. Again, the looped material can be an inherent part of the material of the body or an outer layer of looped material separate to the flexible resilient material can be provided. In an alternative embodiment, the body can present a hook material over its outer surface. However, a looped material is preferred as it is manufacture stretchy looped materials.

The main support material which also provides a looped outer surface 110 can be a synthetic rubber, such as neoprene, having a thickness of approximately 3 mm and lined with stretch nylon on one side and a looped fabric on the other side to which a hook type material can be releasably attached. A suitable material is available from Lomo Industries Ltd.

As described above, the construction of rear fastener panel 216 is slightly different in that it has a hook material on its inner facing surface (opposite to that shown in FIG. 2). This allows the fastener panel to form a releasable fastener by the hooks on its inner facing surface interacting with the outer loop surface of rear panel 218 and possibly rearward side panel 214 to secure the neck orthosis about the patient's neck.

The plurality of panels 202 are joined together to form the neck orthosis. A flat seam is formed by butting the edges of adjacent pairs of panels and then joining the panels together using a flat stitch (e.g. stitching 112 joining front panels 204, 206 in FIG. 1). The plurality of panels can be joined in other ways, for example using bonding, stitching, heat jointing or ultrasonic welding. This provides a substantially flat seam and hence helps to avoid pressure points on the patient's skin. The top and bottom edges are also finished with overlock stitching (e.g. stitching 114). As mentioned above, the top edge can be stiffened to decrease the amount of flex in the material locally and adjacent the top edge. This can be done by incorporating a length or lengths of braided polyester-acrylic cord. The cord can be continuous along the top edge or can terminate to either side of a chin region. The flexible cord or ribbon exhibits resistance to tensile loads that reduces or eliminates the stretch in the material of the neck orthosis adjacent the top edge.

Figure 3:
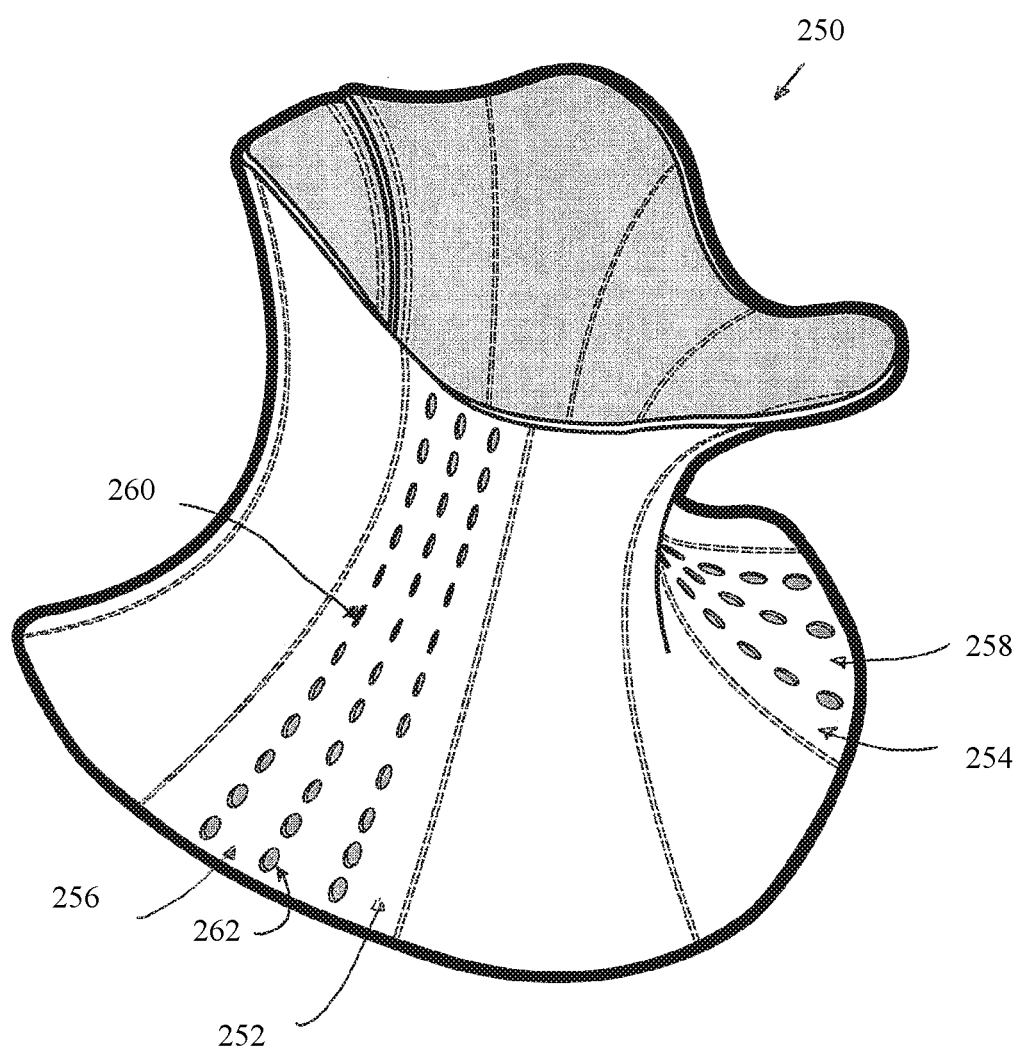
FIG. 3 shows a schematic perspective view of second embodiment of a neck orthosis according to the invention.

FIG. 3 shows a perspective view of a second embodiment of a neck orthosis 250 also according to the invention. The neck orthosis 250 is similar to neck orthosis 100 other than also including a plurality of apertures which provide ventilation slots and provide ventilation and can also improve fit to the wearer. As illustrated in FIG. 3, the forward side panels 252, 254 each include a plurality of apertures 256, 258 arranged generally in a twelve by three array. Each aperture, e.g. aperture 260, has the form of a slit or slot which can deform into a generally circular, oval or curved shape, e.g. aperture 262, as the material of the orthosis is stretched.

Figure 4:
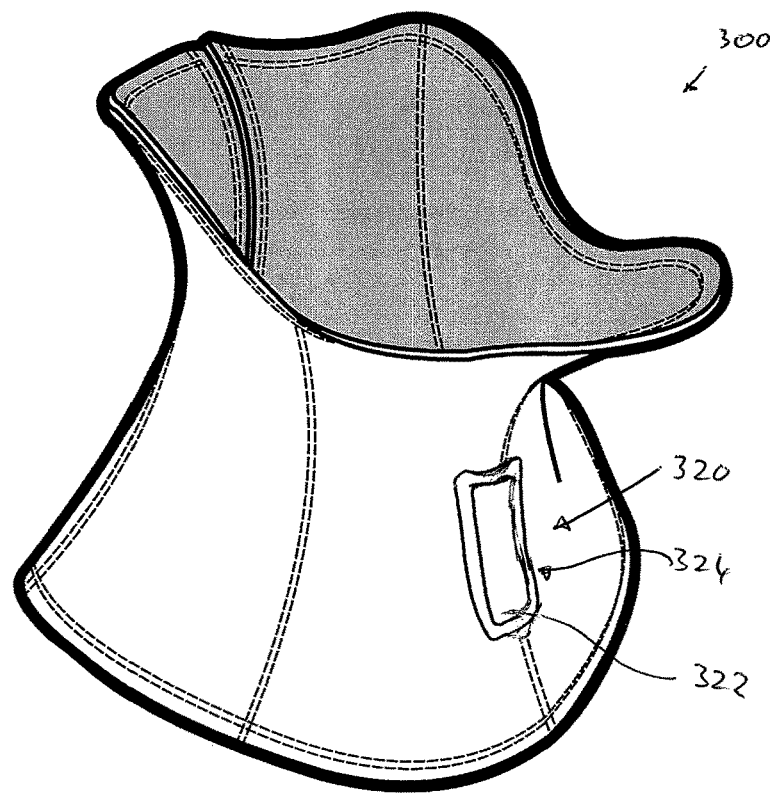
FIG. 4 shows a schematic perspective view of third embodiment of a neck orthosis according to the invention.

FIG. 4 shows a perspective view of a third embodiment of a neck orthosis 300 also according to the invention. The neck orthosis 300 is similar to neck orthosis 100 and also including a larynx pressure relief feature 320. The larynx pressure relief feature 320 helps to reduce or remove any pressure exerted on the larynx of the patient while wearing the neck orthosis. In the illustrated embodiment, the larynx pressure relief feature is in the form of an elongate aperture 322 extending along the inferior-superior axis and generally in the shape of a lozenge or rounded rectangle. It can have a width of between about 3 cm and 5 cm and a length between about 5 cm and 10 cm depending on the size of the intended user. The aperture 322 is surrounded around its periphery by a support 324 in the form of a strip of material which is relatively stiffer than the remainder of the neck orthosis material thereby maintaining the support behaviour of the remainder of the neck orthosis. Hence, the semi-rigid peripheral support 324 transfers load to the remainder of the material.

Neck orthosis 300 also differs from the first embodiment in that it is constructed form merely six panels, comprising a pair of front panels, a pair of side panels and a pair of rear panels. The panels are similar to those shown in FIG. 2 and in particular are cut to provide the same upper edge and lower edge profiles for the neck orthosis 300.

Figure 5:
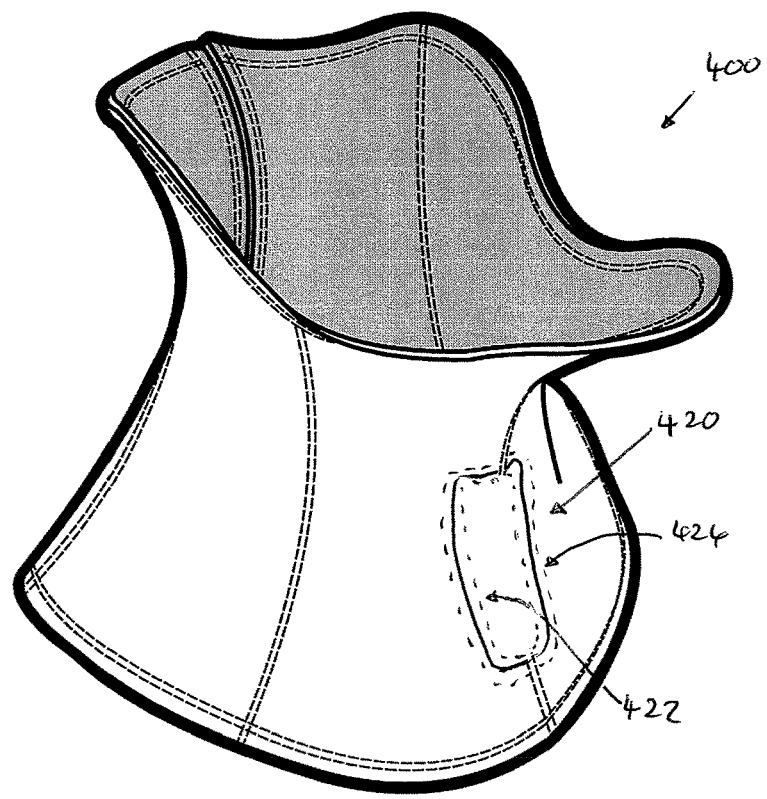
FIG. 5 shows a schematic perspective view of fourth embodiment of a neck orthosis according to the invention.

FIG. 5 shows a perspective view of a fourth embodiment of a neck orthosis 400 also according to the invention. The neck orthosis 400 is also similar to neck orthosis 100 and, similarly to orthosis 300, also includes a larynx pressure relief feature 420. The larynx pressure relief feature 420 helps to reduce or remove any pressure exerted on the larynx of the patient while wearing the neck orthosis. In the illustrated embodiment, the larynx pressure relief feature is in the form of an elongate piece of material 422 extending along the inferior-superior axis and generally in the shape of a lozenge or rounded rectangle. The piece of material can have a width of between about 3 cm and 5 cm and a length between about 5 cm and 10 cm depending on the size of the intended user. The piece of material 422 is attached around its periphery by stitching 424 to the remainder of the neck orthosis material. The piece of material 422 is arranged to reduce pressure exerted on the larynx of the user. For example, the piece of material may be easier to stretch than the remainder of the material so that it can deform to conform to the user's larynx without exerting potentially harmful pressure. Additionally, or alternatively, the piece or material 422 can be engineered to be held away from the user's larynx, by virtue of its three dimensional shape.

Figure 6:
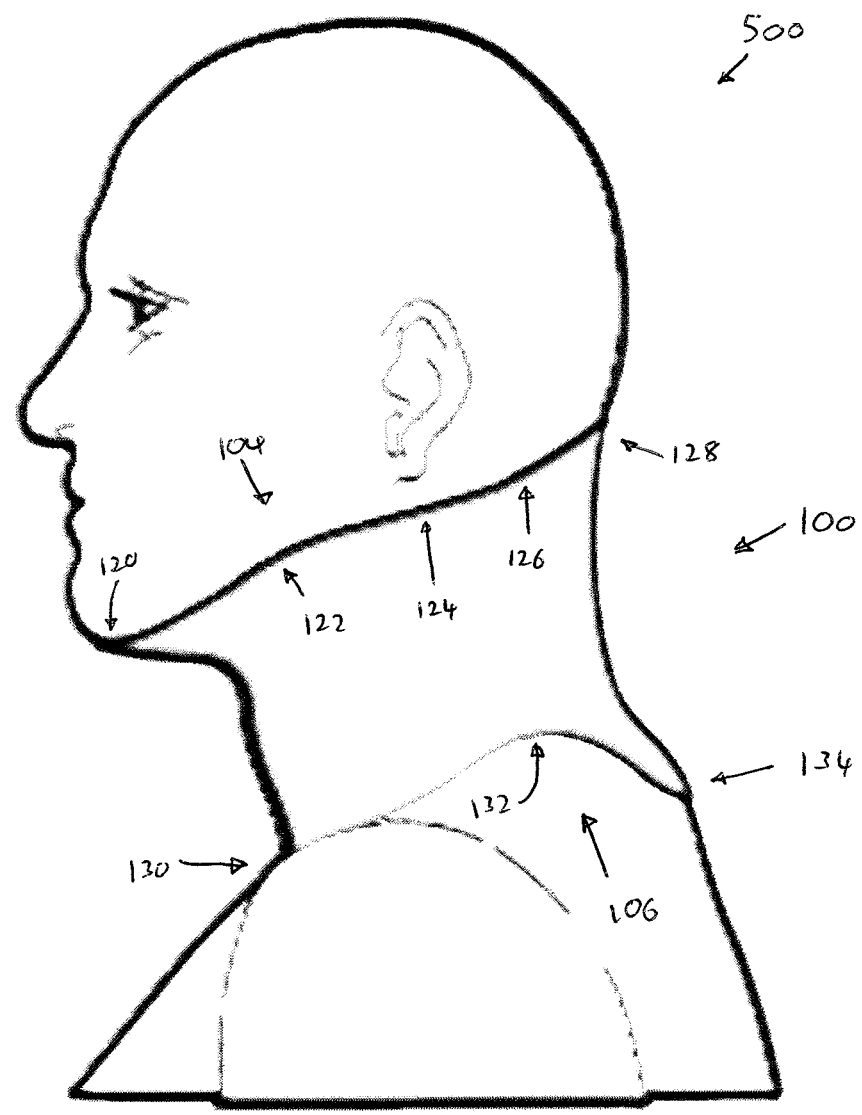
FIG. 6 shows a side view of the neck orthosis of FIG. 1 secured about the neck of a patient in use.

FIG. 6 shows a side view of the neck orthosis 100 secured in use about the neck of a patient 500. As explained above, the top edge 104 and bottom edge 106 of the neck orthosis 100 have non-uniform shape and are configured to engage the user's anatomy immediately adjacent to the patient's neck in the superior and inferior directions. It will be appreciated that the top and bottom edges are symmetric about the patient's medial plane.

The top edge 104 includes a first portion 120 shaped to receive and engage the chin. This chin engaging portion 120 allows a user to speak and eat while also providing a degree of support. It also helps to prevent ingress of the chin into the neck orthosis.

The top edge 104 also includes a second portion 122 shaped to engage and follow the mandible. This mandible engaging portion 122 allows use of the lower jaw while also providing a degree of support.

The top edge 104 also includes a third portion 124 shaped to pass below the patients ear. This ear clearance portion 124 provides comfort of fit and maintains hearing ability by not passing over the ears and allows reduces the amount of material in contact with the patient's skin. A fourth rising 126 portion extends from the ear clearance portion 124 upwardly behind the ear toward a fifth portion 128 arranged to pass around the base of the skull near the occipital base. This skull base portion 128 provides support to maintain the posture of the patient's head.

The bottom edge 106 includes a first front portion 130, a second side or lateral portion 132 and a third rear portion 134.

The first portion 130 is curved and projects downwardly in an inferior direction toward the upper sternal region of the chest. This upper chest engaging portion 130 provides some material engaging the upper chest of the patient which rests on the sternum and extends below the clavicles and can terminate between the sternal notch and the xiphisternum. This portion helps to distribute loads caused by the head tilting forward over the patient's upper chest and provides a land area for subsequently affixed support structures.

A second portion 132 has a generally arched from and extends smoothly upwardly to match the shape of the mid-shoulder passing over the clavicle approximately ⅔ along its length. This lateral portion 132 does not extend greatly laterally along the shoulder but rather passes over the trapezium area closer to the patient's neck so as to allow full movement of the patient's shoulder.

Finally, a third rear portion 134 extends in an inferior direction and passes over the top two or three vertebrae of the thoracic region of the spine. This upper back or thoracic engaging portion helps to maintain correct posture of the patient's head and provides a land area for subsequently affixed support structures.

As illustrated in FIG. 6, in use, the neck orthosis can be secured in a slightly tensioned state by wrapping it about the patient's neck and securing it thereabouts by overlapping rear closure panels 216 and 218 and attaching the hooks on the inner face of panel 216 to the loop material presented on the outer facing surface of the neck orthosis. As noted above, in other embodiments, forward or side opening and closing of the neck orthosis can be provided by changing the pair of adjacent panels which acts as the closure panels.

The shape of the top and bottom edges together with the resiliently deformable, flexible material of the neck orthosis means that the neck orthosis can snuggly fit to the patient's neck and adjacent anatomy to provide a suitable degree of support to the patient's head for an early stage of a medical condition while still allowing some normal functioning, such as talking and eating. The neck orthosis also has a high degree of comfort and can be worn for extended periods of time as the inner surface and other materials of the neck orthosis are designed to reduce or avoid irritation to the patient's skin. Also, the construction of the neck orthosis helps to reduce or avoid pressure or wear sores from forming owing to details of its construction (such as flat seams) and also owing to its shape being performed to engage only specific pre-selected areas of the patients anatomy adjacent the neck.

The entire outer surface 110 of the neck orthosis presents a loop material which forms a part of a hook-and-loop fastening system by which a plurality of support members can be releasably attached to the neck orthosis so as to customise the support that can be provided to the current and specific needs of an individual patient. At a first or initial stage of a medical condition, the neck orthosis 100, 250, 300, 400 alone can be used to provide appropriate support. However, as the medical condition progresses, or if the neck orthosis is first introduced at a later stage of severity of the condition, then one or more support members can be releasably attached to the neck orthosis. Hence, the invention also provides a head support system which uses the neck orthosis as a common foundation to which a plurality of support members of the same or different types can be releasably attached to provide support to the patient's head appropriate to the current state of the patient's medical condition.

Each support member can be attached to the neck orthosis at a plurality of positions and the plurality of positions is continuous rather than discrete. Hence, the position at which the support member is, or support members are, attached is not pre-determined, but rather is determined by each user. Hence, the nature of the support provided can be more precisely tailored for each individual and/or can be changed as the condition of the individual changes.

In other embodiments less than the entire surface of the neck orthosis can present hook or loop fastener material. Also, the outer surface of the neck orthosis can have one or more regions of hook or loop fastener material for example, on either side, at the front and/or at the rear. However, a sufficiently large region or regions of hook or loop fastener material still provides a plurality of positions at which the support members can be releasably attached and which positions are continuous rather than discrete. Hence, the position and/or orientation of attachment of the support member can be determined by the user or their medical practitioner rather than being predetermined by the construction of the neck orthosis.

FIGS. 7A and 7B show perspective views of a first type of support member 600, 620. The first type of support member 600, 620 is a generic support member which can be releasably attached at any position over the outer surface 110 of the neck orthosis to provide customised or tailored support for the patient during a second stage of the medical condition in which more support is required than in the first stage. The first type of support member 600, 620 has the general shape of a long, thin, narrow member, such as a slat, splint or thin bar. It can have a length of between about 5 cm and 15 cm, a width of around 1 cm to 2 cm and a thickness of a few millimetres, depending on the material from which it is constructed. The first type of support member has a central core 602, 622 which provides the support properties and an outer covering of a material 604, 624 which has a plurality of hooks on a first orthosis contacting side 606, 626 and a plurality of loops on a second outward facing side 608, 628. The plurality of hooks are arranged to co-operate with the loops presented by the outer surface 110 of the neck orthosis so that the first type of support can be releasably attached thereto. A suitable material for the hook type material is the Hook 088 product provided by Velcro Europe S.A. A suitable material for the loop type material is a Velcro sew on loop type material available in roll form from A & N Trimmings Limited.

Different types of the first type of support member can be provided by changing the properties of the core 602, 622. A rigid support member 600 can be provided by making the core 602 from a rigid material which can maintain the required level of support under the loads that would typically be experienced when supporting a typical human head. These static supports can be made from a variety of metals or plastics. For example, a suitable plastic is acrylonitrile butadiene styrene (ABS). The core can be permanently deformed to a generic shape (e.g. curved) or custom formed to a specific shape to fit an individual user.

A flexible support member 620 can be provided by making the core 622 from a resiliently flexible material which can provide a level of support but can also flex under the loads that would typically be experienced when supporting a typical human head so as to allow a greater degree of movement. For example, as illustrated in FIG. 6B, the support member 620 can be resiliently deformed between a first configuration and a second configuration 628 (shown in ghost lines). These dynamic supports can be made from a variety of metals or plastics. For example, the core can be die cut from a polypropylene, such as homopolymer polypropylene (PPH/PP-DWST) available from Direct Plastics Limited). A suitable metal is a spring steel, such as an unalloyed, medium carbon spring steel.

The head support system can include, for example, twenty of the first type of support member, ten rigid and ten dynamic. This allows the support provided by the neck orthosis to be customised or otherwise tailored to the patient's current and evolving requirements. For example, FIG. 8 shows a perspective view of an assembly 700 formed from the head support system of the invention and including the neck orthosis 100 and four of the first type of support member. A first static support member 701 is releasably attached to the neck orthosis generally in the anterior-posterior direction and has a patient specific shape so as to provide enhanced support to the patient's head in that direction. Second to fourth dynamic support members 702, 704, 706 and then releasably attached over the first support member 701 to the neck orthosis to provide a greater degree of flex and movement to the patient's head in the lateral direction. It will be appreciated that as the outward facing surface of the support member 701 is made of a loop material, the hooks on the undersides of support members 702, 704 & 706 will also releasably fasten to support member 701, as well as the outer surface of neck orthosis 100, thereby increasing the strength of attachment.

Figure 9A:
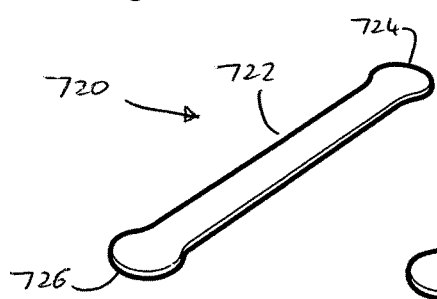
FIGS. 9A, 9B and 9C show respective perspective views of a further embodiment of a first type of support member.
Figure 9B:
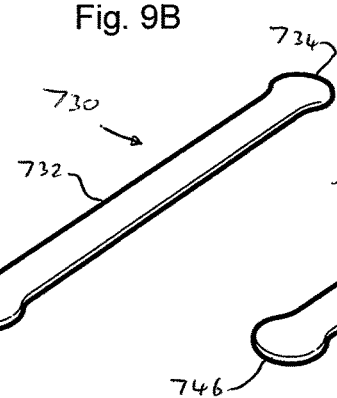
Figure 9C:
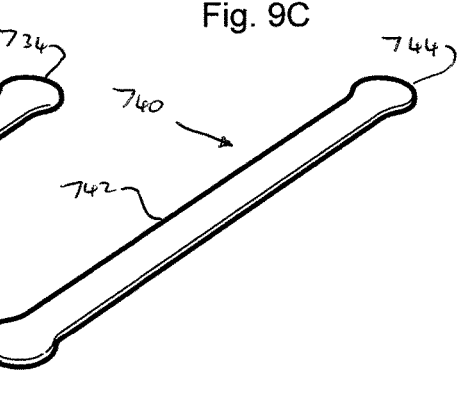

FIGS. 9A, 9B and 9C show respective perspective views of a further embodiment of the first type of support member 720, 730, 740. The further embodiments 620, 730, 740 of the first type of support member are also a generic support member which can be releasably attached at any position over the outer surface 110 of the neck orthosis to provide customised or tailored support for the patient during a second stage of the medical condition in which more support is required than in the first stage. The further embodiment is generally similar to the first embodiment, but has a different overall shape. The further embodiments a body, 722, 732, 742, with an extended head portion 724, 734, 744 at a first end and an extended foot portion 726, 736, 746 at a second end. The head and foot portions are each in the form of a disc extending continuously from the body which again has the general shape of a long, thin, narrow member, such as a slat, splint or flat stick. As illustrated in FIGS. 9A to 9C the further embodiments have different lengths of approximately 12 cm, 15 cm and 19 cm respectively.

Figure 9D:
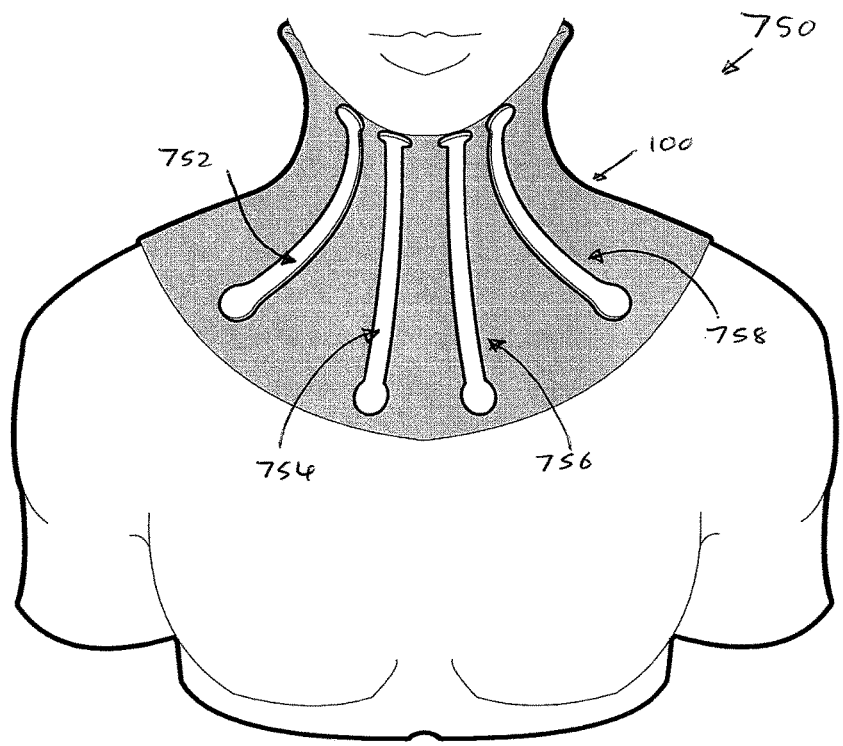
FIG. 9D shows a perspective view of an assembly of a support system according to the invention including a plurality of the first type of support member illustrated by FIGS. 9A-9C.
Figure 9E:
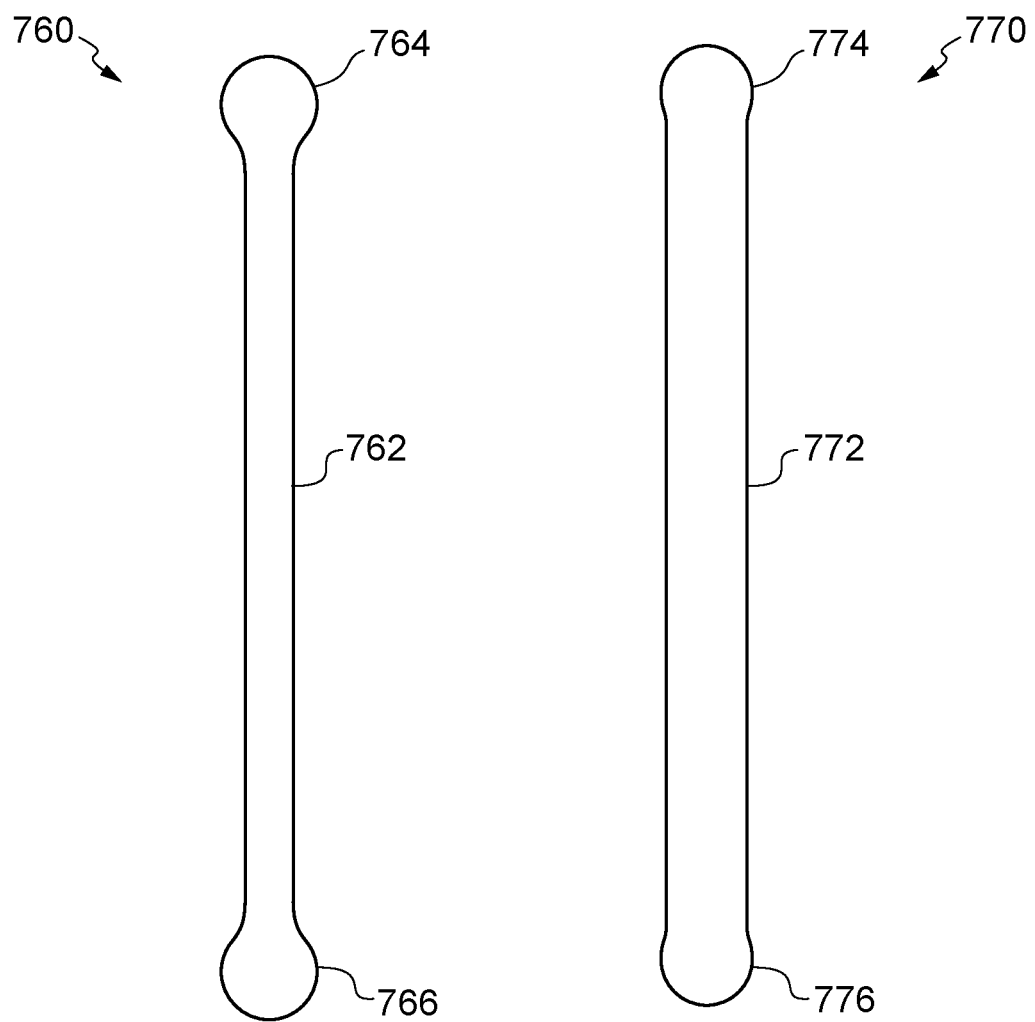
FIG. 9E show respective views of different strength versions of the further embodiment of the first type of support member.

FIG. 9E shows two different support strength versions of the further embodiment of the first type of support member. The first type of support member can be provided in two different versions which provide different levels of support. A first version 760 may provide less support and may be used when the user requires minimal support, for example at an early stage of neck weakness. A second version 770 may provide more support and may be used when the user requires a greater degree of support for example when the user is suffering from more severe neck weakness.

As illustrated in FIG. 9E, the two versions have generally the same construction other than their width. The first version 760 has a main body 762 with a circular part 764, 766 at each end. The overall length can be about 188 mm, the diameter of the circular parts 764, 766 can be about 18 mm, the thickness can be about 2 mm and the width of the main body 762 can be about 8 mm. Similarly, the second version 770 has a main body 772 with a circular part 774, 776 at each end. The overall length can be about 188 mm, the diameter of the circular parts 774, 776 can be about 18 mm, the thickness can be about 2 mm and the width of the main body 772 can be about 16 mm. As the width of the main body is greater for the second version compared to the first version, it provides a stiffer support member. The construction can be similar to other support members with a central core made from polypropylene and an outer covering of a hook or loop fastener material.

Although the first and second versions are shown in FIG. 9 with a single length, different lengths of the first and second versions can be provided in the same manner as described above with reference to FIGS. 9A to 9C.

FIG. 9D shows a perspective view of an assembly 750 formed from the head support system of the invention and including the neck orthosis 100 and four 752, 754, 756, 758 of the further embodiments of the first type of support member. The four support members 752-758 are arranged generally symmetrically on either side of the patient's neck so as to provide enhanced support to the patient's head in the anterior-posterior direction. It will be appreciated that as the outward facing surfaces of the support members 752-758 are made of a loop material, the hooks on the undersides of further support members can also be releasably fastened over the support members 752-758, as well as the outer surface of neck orthosis 100, thereby increasing the strength of attachment.

It will be appreciated that other positions, arrangements, and combinations of types of the first type of support member can be used depending on the support required by any particular patient. Indeed, the nature and degree of support available using the invention is fully adjustable and customisable. For example, the support system can be used to provide asymmetric support, for example, on only one side or in only one direction. This may be appropriate for patient's that have suffered strokes or for patients in which only a part of the brain, nervous system or muscles are affected.

As well as the generic support members 600, the head support system can include specific support members which are configured to be releasably attached to the neck orthosis to provide a specific type of support. Further Figures illustrate a plurality of different specific support members which will now be described in greater detail. The construction of the specific support members is generally similar to that of the generic support members in that they include a core of a material providing either a rigid or a dynamic support and have an outer coating of at least a hook type material by which they can be releasably attached to the neck orthosis. These specific supports can be used during a second stage of the medical condition which is more severe than the first stage or which otherwise has different head support requirements to the first stage.

Figure 10A:
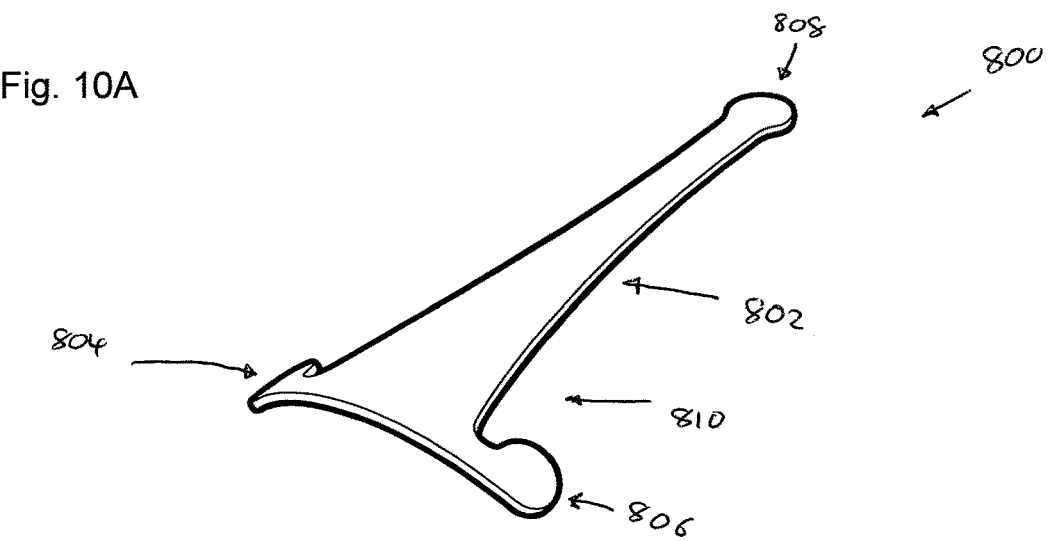
FIG. 10A shows a perspective view of a second type of support member.

FIG. 10A shows a perspective view of a first type of specific support member 800 which is a shoulder or lateral support member. The lateral support member has a generally triangular body 802 with a disc shaped land 804, 806, 808 at each corner. The lands provide a greater contact area for securing the support to the neck orthosis. A first end portion of the support 810 is curved along its shorter transverse axis so as to accommodate the shape of the patient's shoulder in use. As illustrated in FIG. 10A the support 800 may not be curved along its longer longitudinal axis when not in use, but in other embodiments the support may also be curved along its longitudinal axis also so as to accommodate the shape of the patient's neck if the support is made from a rigid or less flexible material.

Figure 10B:
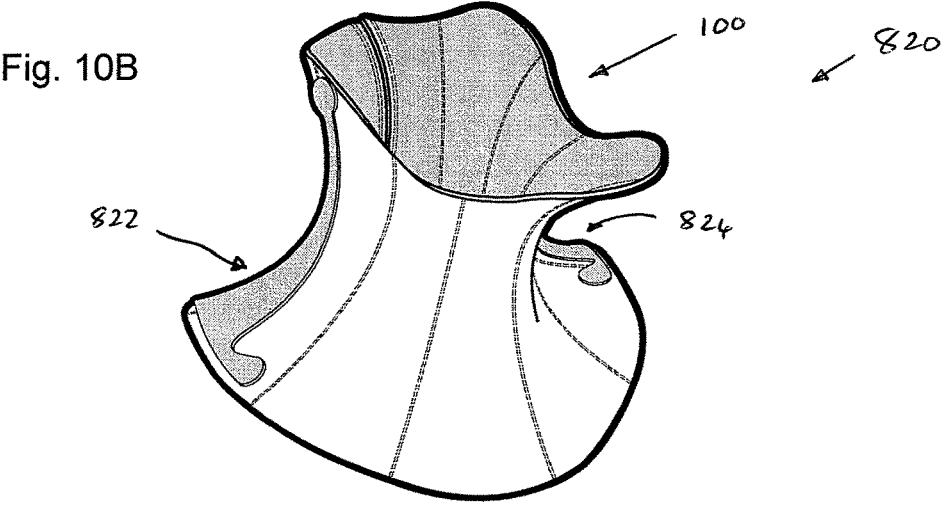
FIG. 10B shows a perspective view of an assembly of a support system according to the invention including a plurality of the second type of support member illustrated by FIG. 10B.
Figure 10C:
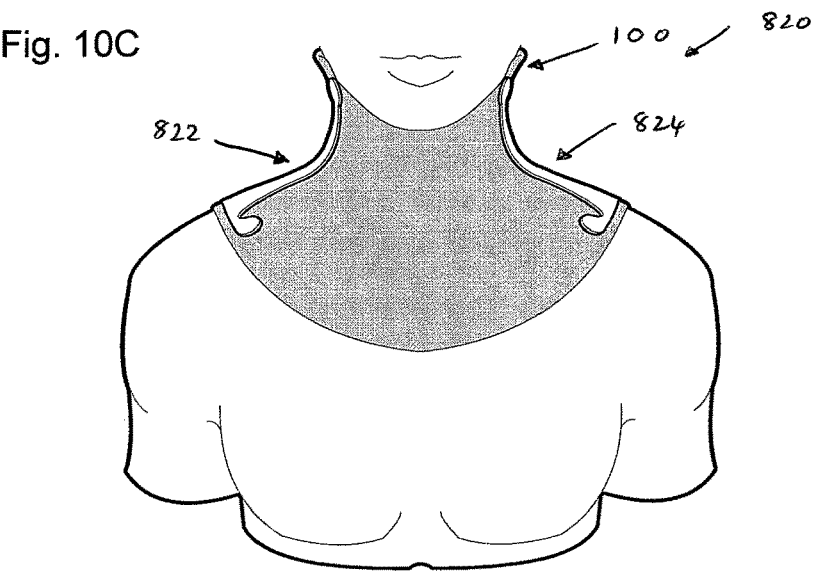
FIG. 10C shows a front view of the assembly of FIG. 10B about the neck of a patient in use.

FIG. 10B shows a perspective view of an assembly 820 formed from the head support system of the invention and including the neck orthosis 100 and a pair of lateral supports 822, 824. FIG. 10C shows a front view of the assembly 820 in use about the neck of a patient. The lateral support members 822, 824 are arranged generally symmetrically on opposed sides of the patient's neck so as to provide enhanced support to the patient's head in the medial-lateral direction. The shoulder support members 822, 824 curve smoothly along a longitudinal axis to match the shape of the transition between the patient's neck and shoulder and also curves in a transverse direction so as to match the curve of the patient's shoulder arch to avoid rubbing injuries. One or a pair of shoulder supports can be provided to provide support to the left and/or right side of the neck. The lateral supports 822, 824 can be constructed similarly to the generic supports with an inner core and outer coatings of a hook type material on an inner facing side and a loop type material on an outer facing side.

The first end region of the of the lateral support intended to engage the patient's shoulder in use can include a pressure relieving substrate on an underside such as a gel or other form of padding. A suitable material is MaxaCane Gel as provided by A Algeo Ltd.

Figure 11A:
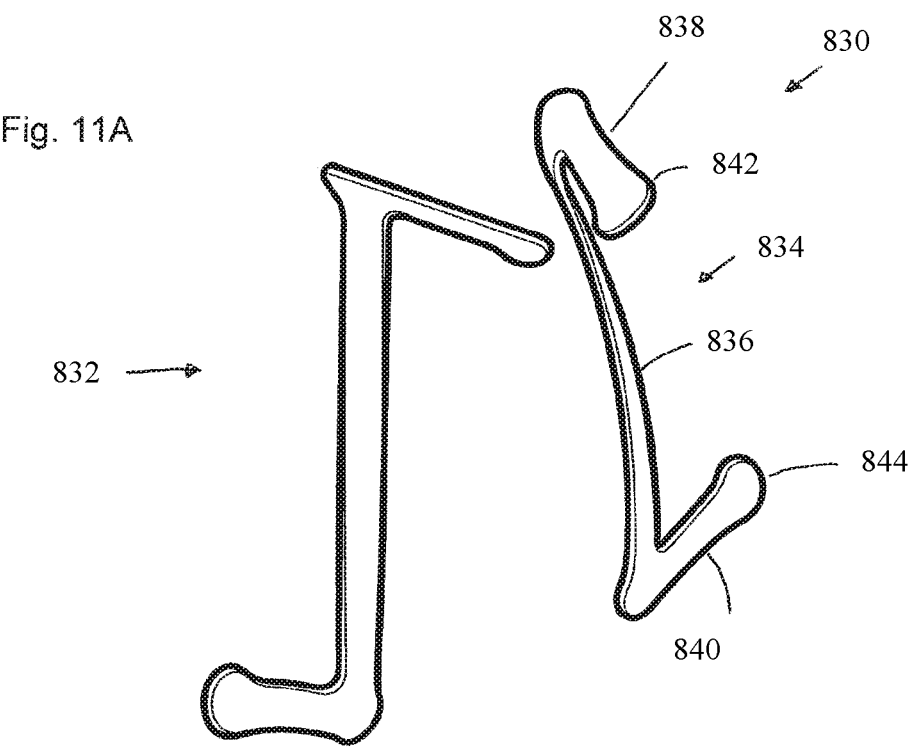
FIG. 11A shows a perspective view of a pair of third type of support member.
Figure 11B:
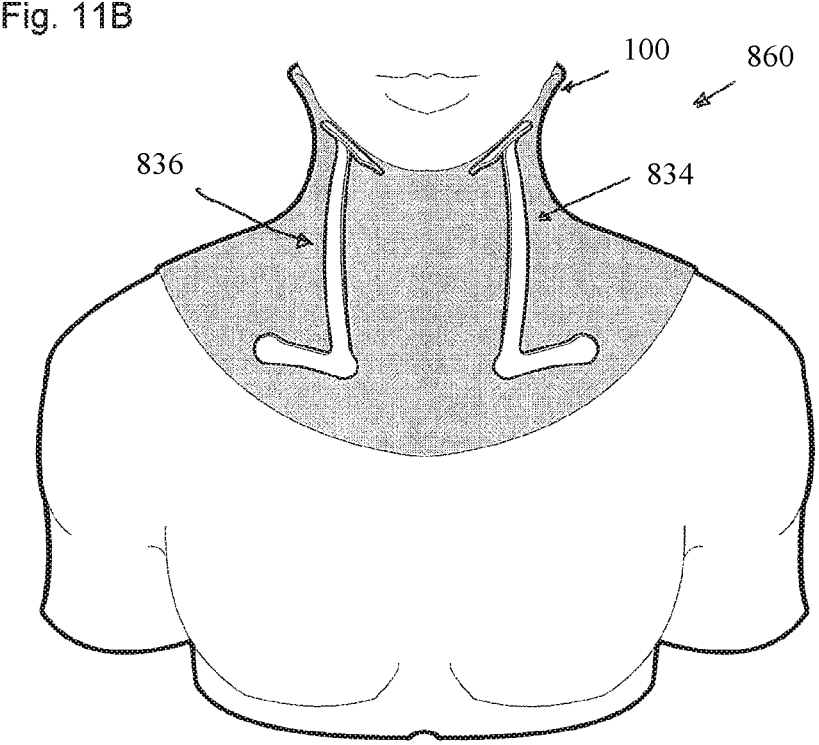
FIG. 11B shows a front view of an assembly including the pair of the third type of support member of FIG. 11A about the neck of a patient in use.

FIG. 11A shows a perspective view of a pair 830 of a second type of support member 832, 834 which is a lower jaw or mandible support member and is generally shaped to match the shape of the patient's lower mandible and the patient's neck immediately adjacent thereto. In FIG. 11A the second type of support is each shown in an in use configuration as also illustrated in FIG. 11B which shows a front view of an assembly 860 of the head support system of the invention comprising the neck orthosis 100 and the pair of second type of support members 832, 834 releasably attached thereto. In use the second type of support member provides head support in a posterior direction and also provides support in a superior direction for patients suffering jaw drop.

The jaw support 834 has a generally zig-zag or Z shape with a central member 836 having an upper member 838 extending transversely in a first direction from a first end and a lower member 840 extending transversely in a second direction from a second end. Respective free ends of the upper 838 and lower 840 members bear disc shaped lands 842, 844. The lower member is slightly curved to match the shape of the upper chest adjacent the neck as illustrated in FIG. 11B. The central member 836 can twist or be twisted along its longitudinal length and the upper member 838 can be tilted at its joint with the central member and can also be curved along its longitudinal axis to accommodate the shape of the patient's jaw or mandible, as best illustrated in FIG. 11B. Similarly to the first type of support, padded regions can be provided on the underside of the second type of support on the jaw/mandible engaging portion 838 and/or on the chest engaging portion 840. The other support 832 of the pair has the same shape but is a mirror image of the other. That is, each support of the pair of supports has a handedness as, although they have the same shape, they have loop type material and hook type material on differing opposite sides so that one 832 is a right hand jaw support and the other 834 is a left hand jaw support. The second type of support member also has generally the same constructions as the other support members of an inner core with coatings of hook and loop type material.

Figure 12:
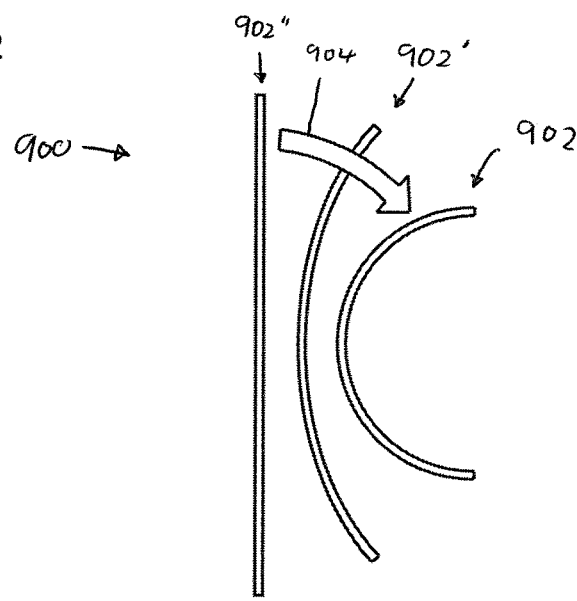
FIG. 12 shows a side view of a fourth type of support member passing between a rest state, partially tensioned and fully tensioned state.

FIG. 12 shows a side view of a third type of support member 900 which is arranged to provide a reverse bias. The third type of support member is similar in construction to the generic support member 600 in that it is in the form of a slat or thin flat bar, but it is also provided as a leaf spring in which its normal or non-tensioned state 902 is curved. In FIG. 12, the support member is shown in a loaded, tensioned state 902" in which it is straight and also in an intermediate partially loaded and tensioned state 902'. Arrow 904 shows the direction of the force exerted by the support member 900 when loaded away from its un-tensioned state 902. This leaf spring type support member can be used to pre-load the neck orthosis with a biasing force so as to provide enhanced support to the patient's head which tends to act against the force being applied by the support member 900.

Figure 13:
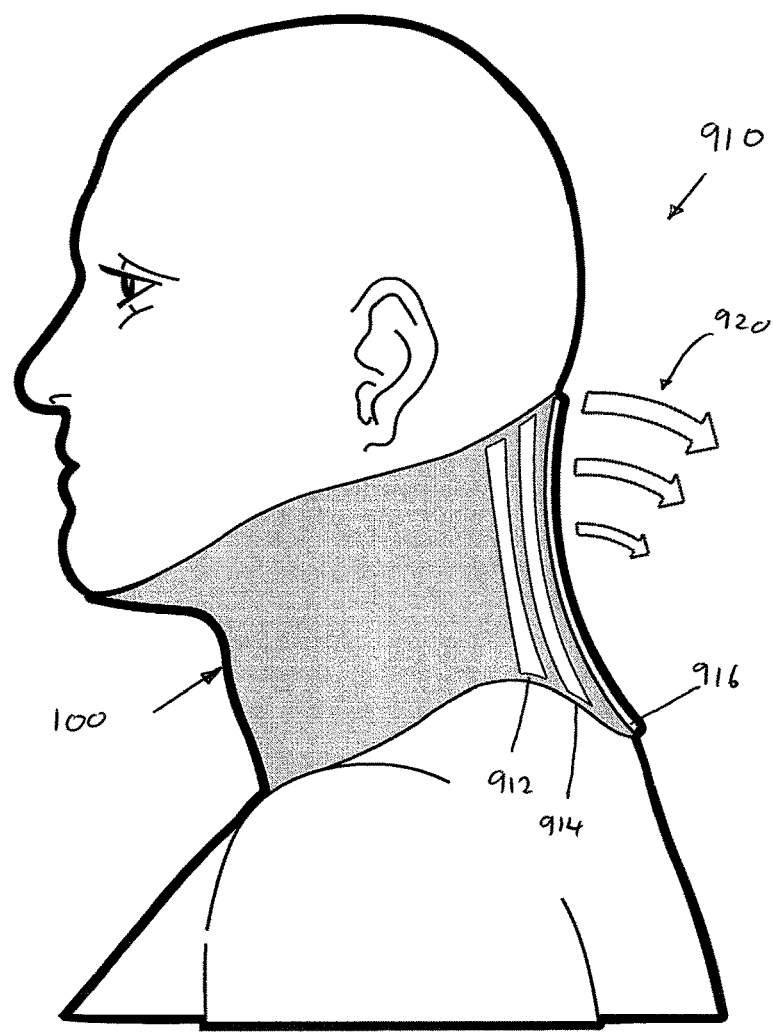
FIG. 13 shows a side view of a further assembly of a support system according to the invention including a plurality of the fourth type of support members as shown in FIG. 12.

FIG. 13 shows a perspective view of an assembly 910 of the head support system of the invention comprising the neck orthosis 100 and a three 912, 914, 916 of the third type of support member releasably attached thereto toward the rear of the neck orthosis. The support members 912, 914, 916 are attached to the neck orthosis in a tensioned state (i.e. straightened compared to their un-tensioned state) and therefore apply a force in the direction illustrated by arrows 920 so as to pull the patient's head in a posterior direction owing to the tension in the springs causing them to try and return to their un-tensioned state. Hence, the support members can be attached to the neck orthosis 100 in a tensioned state so that they exert a counter acting force to at least partially restore the patient's head to its normal or preferred posture.

Figure 14A:
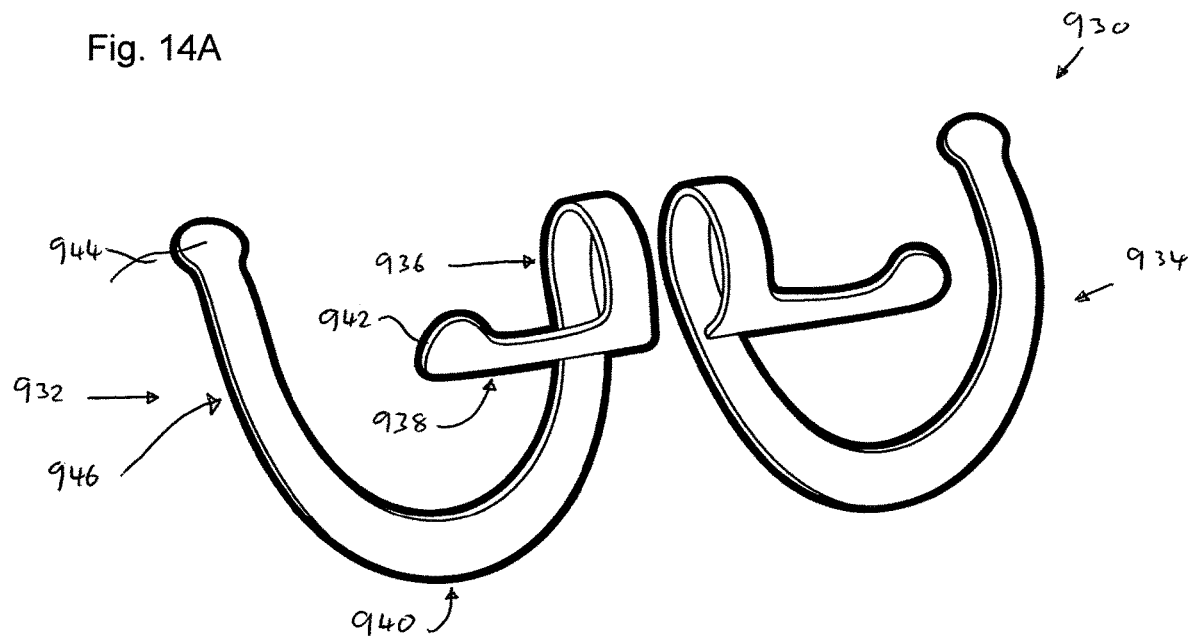
FIG. 14A shows a perspective view of a pair of fifth type of support member.
Figure 14B:
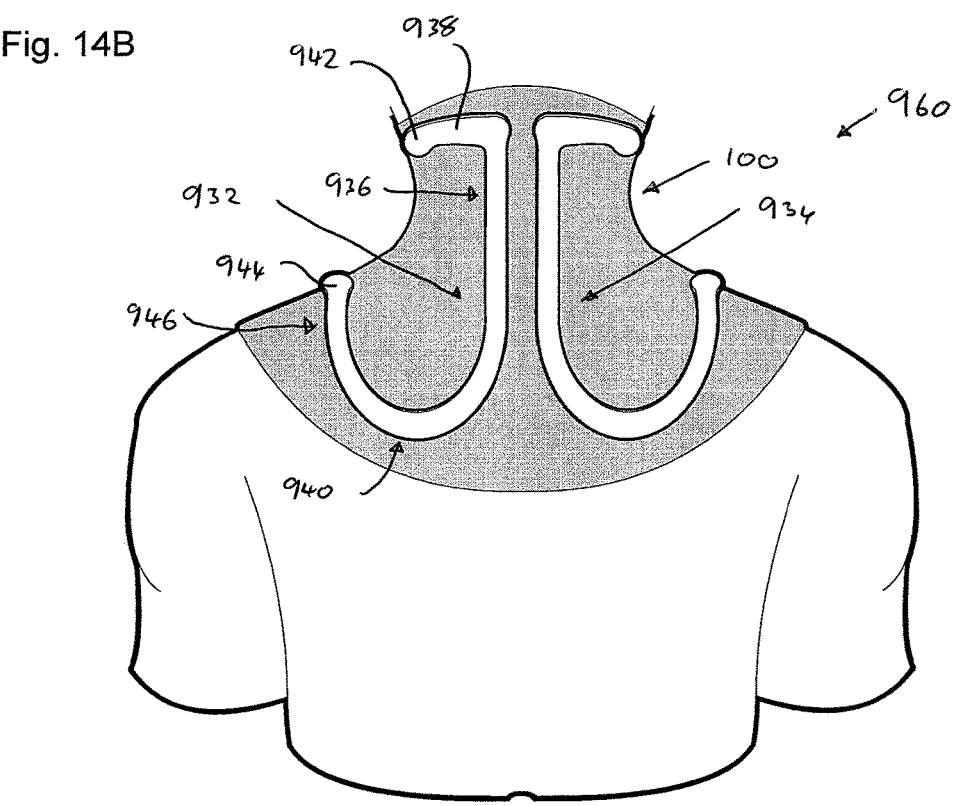
FIG. 14B shows a rear view of an assembly including the pair of the fifth type of support member of FIG. 14A about the neck of a patient in use.

FIG. 14A shows a perspective view of a pair 930 of a second embodiment of the third type of support member 932, 934 which are also reverse biased and in their un-loaded or un-tensioned state. The third type of support member 932, 934 which is a back or rearward support member and in particular a spinal support member. FIG. 14B shows a view from the rear of the patient of an assembly 960 of the head support system of the invention in use and comprising the neck orthosis 100 and the third reverse bias type of support member 1002 releasably attached thereto. The third type of support member is a posterior support member and is generally shaped to match the shape of the upper back of the patient and the patient's neck immediately adjacent thereto. In use it provides head support in an anterior direction by acting to pull the patients head in a posterior direction.

The rear support 932 has a generally curved J shape with a linear central member 936 having an upper member 938 extending transversely and linearly in a first direction from a first end and a lower curved member 940 extending transversely in the same first direction from a second end. Respective free ends of the upper 938 and lower curved 940 members bear disc shaped lands 942, 944. A free end portion 946 of the lower curved member 940 is also slightly curved along its local longitudinal axis to match the shape of the rear of the patient's shoulder as best illustrated in FIG. 14B. As best illustrated in FIG. 11A, the central member 936 provides a reverse bias by having a curved unloaded state so that it can act as a leaf spring when tensioned into a less curved or straighter configuration so as to match the local curvature of the patient's spine in the neck region. The upper member 938 can also be curved along its local longitudinal axis to accommodate the shape of the patient's neck or lower skull region, as best illustrated in FIG. 14B.

Similarly to the first type of support, padded regions can be provided on the underside of the third type of support on the upper linear portion 938 and/or on the lower curved portion 940.

The other support 934 of the pair has the same shape but is a mirror image of the other. That is, each support of the pair of supports has a handedness as, although they have the same shape, they have loop type material and hook type material on differing opposite sides so that one 932 is a right hand spinal support and the other 934 is a left hand spinal support. The third type of support member also has generally the same constructions as the other support members of an inner core with coatings of hook and loop type material.

The spinal support supports 932, 934 in use generally adopt a curved form along the longitudinal axis of the central member 936 to match the shape of the rear of the patient's neck and upper part of the spine beginning at the occipital protuberance down to the T2 thoracic vertebra.

Various different types of support members and different combinations of support members can be selected by the user which best suit their requirements. Due to the widely variable nature of the medical condition symptoms, individual sufferers may have very specific and different support needs which are not currently met. The modular support members of the head support system of the invention can be tailored to a personalised specification.

Figure 15:
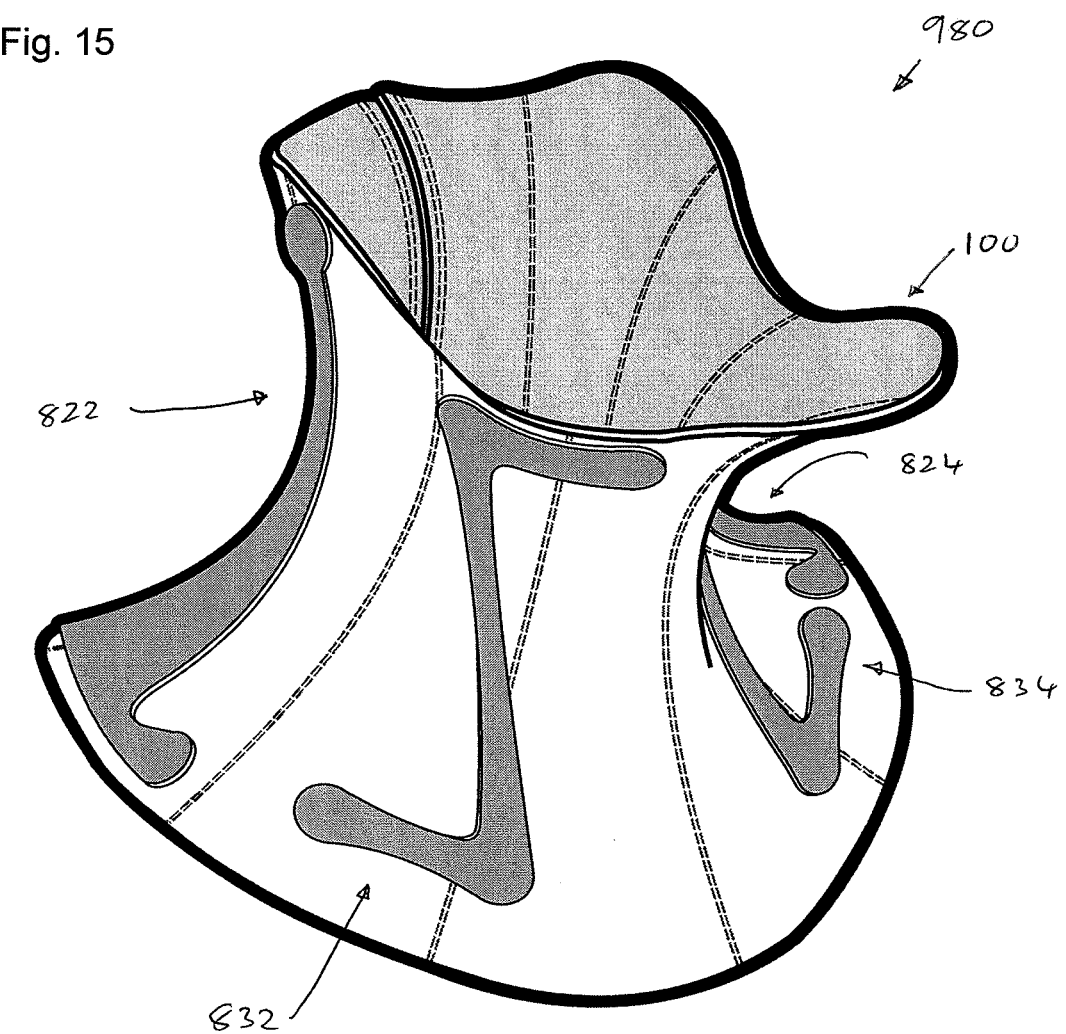
FIG. 15 shows a perspective view of a further assembly of a support system according to the invention including pairs of the second and third type of support member.

For example, FIG. 15 shows a perspective view of an assembly 980 of the head support system of the invention comprising a pair of lateral supports 822, 824 releasably attached to the right and left hand side of the neck orthosis 100 together with a pair of jaw supports 832, 834 releasably attached to the forward right and left hand side portions of the neck orthosis 100. Hence, this assembly provides personalised support for a patient requiring head support to the right and left hand sides and jaw support on both sides.

It will be appreciated that owing to the modular nature of the support members and their releasable attachment to each other and to any position on the neck orthosis very many different combinations and arrangements of support members are possible depending on the patient's individual requirements and that illustrated arrangements are merely examples.

At a further stage of severity of the medical condition, many or all of the different types of support member can be used together. A combination of rigid and flexible support members can be used or only rigid support members. This can provide the maximum possible support for the patient.

Figure 16A:
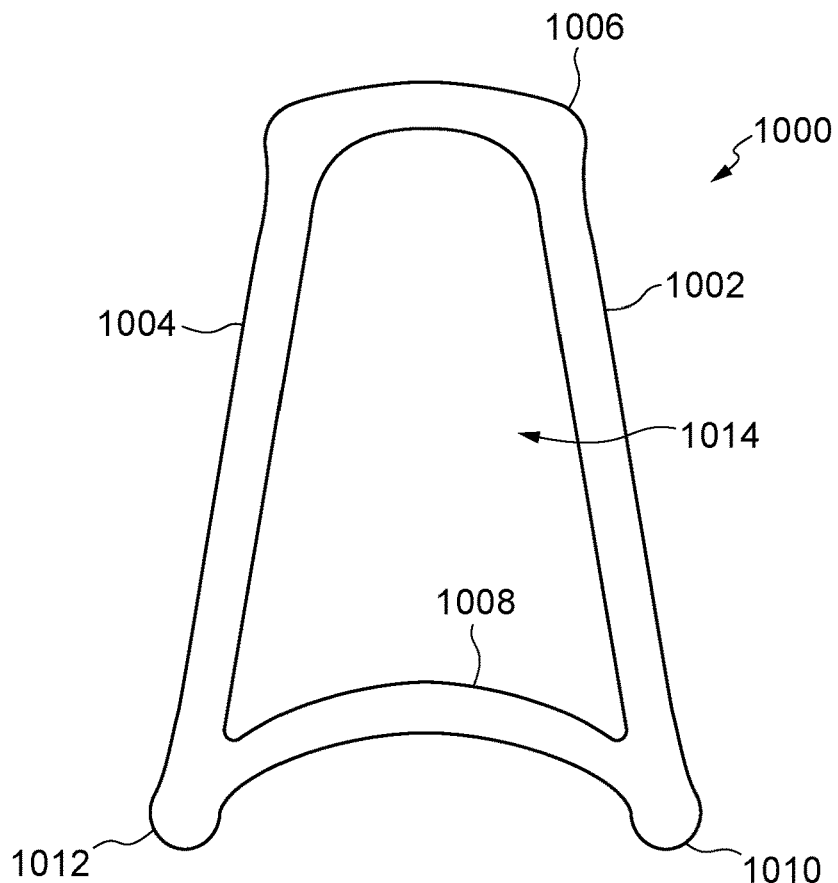
FIG. 16A shows a front elevation of a sixth type of support member.
Figure 16B:
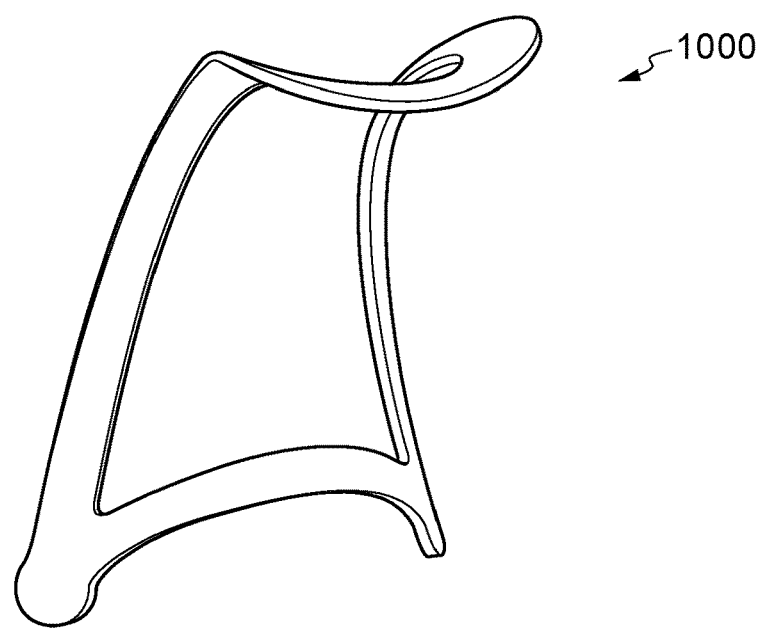
FIG. 16B shows a perspective view of the sixth type of support member.

FIGS. 16A and 16B respectively show a front elevation and perspective view of a sixth type of support member 1000 which is configured to act as a chin support. The Sixth type of support member is generally A-shaped and includes a first 1002 and a second 1004 side member which are joined at their upper ends by an upper cross member 1006 and toward their lower ends by a lower cross member 1008. Lower ends of each side member include generally circular shaped lands 1010, 1012. As best illustrated in FIG. 16B, the chin support 1000 has a complex three dimensional shape so as to appropriately accommodate the patient's neck in use and engage the chin to provide appropriate support. In particular, the chin support is curved about the inferior-superior axis so as to extend around the anterior part of the patient's neck and under the patient's chin. The Chin support is also curved about the medial-lateral axis so as to accommodate the transition between the neck and chin.

The chin support 1000 is designed to fit from the tip of the users chin, then bridge down toward the chest. The chin support is adapted or configured to provide frontal support and is particularly useful in scenarios where the jaw supports are uncomfortable or otherwise unsuitable, for example owing to loss of muscle mass around the jawline. The open area or aperture 1014 defined by the parts of the chin support has the effect of stretching the neck orthosis material to an extent. This can help to relieve pressure from the throat area. In addition this chin support 1000 is configured or arranged to apply pressure to the front of the jaw thereby reducing the effect of "chin droop" and minimising the amount of drool exiting the user's mouth. The contour of the upper chin support cross member 1006 is configured to distribute the weight of the chin over its whole length. This helps to avoid the point loading which can be experienced with rigid chin supports. The first 1002 and second 1004 side members are configured to draw the neck orthosis material away from the user's throat, thereby relieving pressure on the Adams apple.

The chin support is constructed in the same manner as the other supports with a core, for example of polypropylene, and covered in a hook or loop fastener material.

Figure 17A:
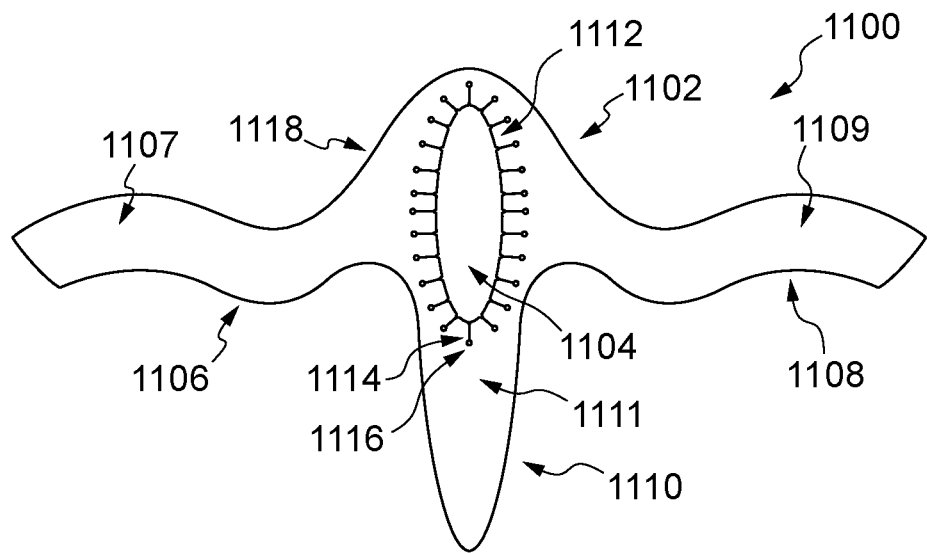
FIG. 17A shows a view of a padding element of the support system in a flat configuration.
Figure 17B:
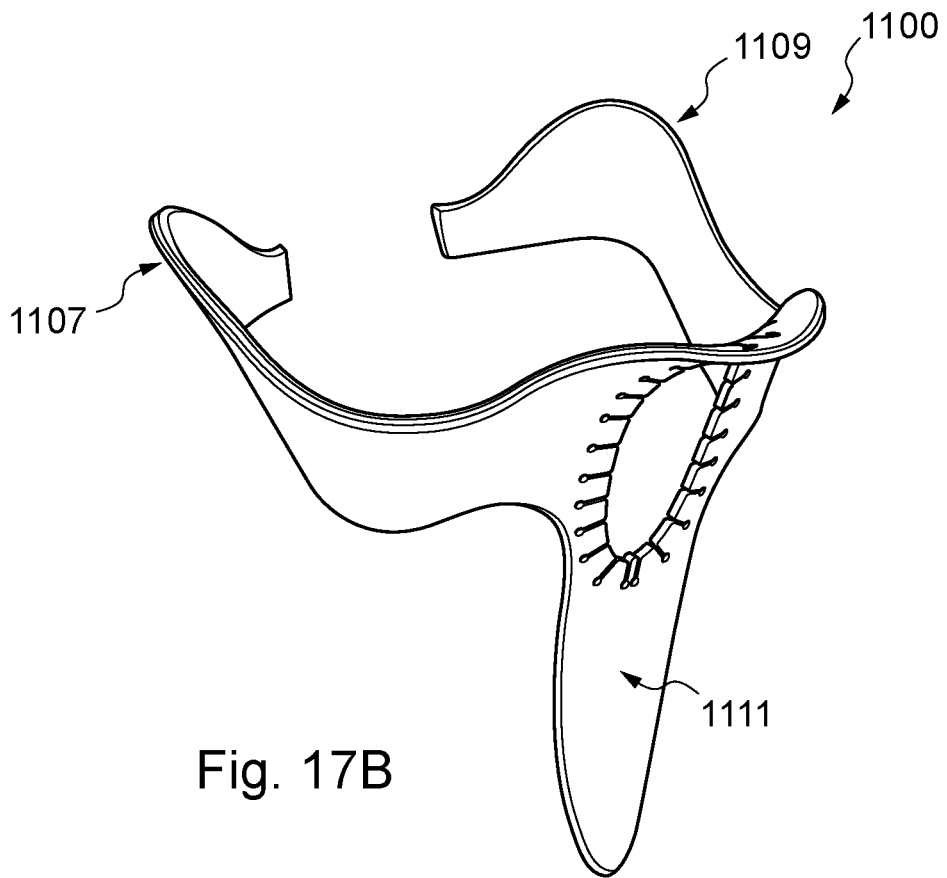
FIG. 17B shows a perspective view of the padding element of the support system in the configuration it will adopt in use.

FIGS. 17A and 17B respectively show a padding element of padding part 1100 of the support system in a flat configuration and the configuration it will adopt in use. The padding 1100 can be provided in addition, or as an alternative, to the pressure relief features of the embodiments of the neck orthosis described above and illustrated in FIGS. 4 and 5. In different embodiments, the padding 1100 can be provided as an integral part of the neck orthosis or as an insert or removable part.

As illustrated in FIG. 17A, the padding 1100 has a body 1102 which defines a central generally oval or ellipse shaped aperture 1104. A first curved arm 1106 and a second curved arm 1108 extend from opposed sides of the body 1102. An intermediate portion 1107, 1109 of each arm is shaped to correlate with respective areas on either side of the user's neck where pressure is most likely to be supplied by some of the support members. An upper edge 1118 of the insert 1100 extends continuously along an upper edge of the first arm 1106, body 1102 and second arm 1108 of the insert 1100. The shape or profile of the upper edge 1118 substantially matches the shape or profile of the corresponding parts of the upper edge of the neck orthosis itself. A tail portion 1110 extends downwardly from a lower part of the body 1102. A portion 1111 of the tail 1110 between the lower edge of aperture 1104 and a free end of the tail 1110 can provide a small degree of support in itself and can also provide additional padding on the upper chest area when support members are attached.

The periphery 1112 of the material of body 1102 which extends around and defines central aperture 1104 includes a plurality of slits or slots e.g., slot 1114, each terminating at a closed end in a small circular hole, e.g. hole 1116. Aperture 1104 is shaped, sized and positioned to relieve any pressure on the Adams apple applied via the neck orthosis when fitted. The slots around the aperture 1104 allow further movement within the structure of the padding element to permit movement of the neck and throat structure during eating, talking, swallowing, etc.

The padding part 1100 is designed to offer additional padding to the areas where the various support members which can be attached to the neck orthosis will apply upward pressure to the patient's anatomy. The padding 1100 incorporates an anterior aperture 1104 positioned, sized and shaped to effectively remove the neck orthosis material away from the user's throat area to reduce or eliminate the sensation of pressure on the Adams apple. As can be seen in FIGS. 17A and 17B the material adjacent the aperture has a series of slots running from its centre, which allows the material of the padded insert to flex and match to the contours of the throat area providing greater comfort. The material of the padded insert can have a degree of stretch to accommodate the contours of the individual. The material can also be breathable to increase comfort and/or reduce heat. A suitable material for the padding 1100 is foam, such as a polyurethane foam, such as Poron Medical Blue OB218 as available from Algeos Ltd.

The padding 1100 can be attached to the main neck orthosis using stitching and with its upper edge profile 1118 level with the upper edge profile of the neck orthosis. In other embodiments, the padding can comprises a foam component within an outer sheath or cover of cotton or similar material and including several areas of hook type material towards the free ends of the arms and the free end of the tail. The hook type material can attach to a loop type material stitched into the corresponding inner face of the neck orthosis as a means of attachment.

In another embodiment, a pocket can be sewn into, or otherwise provided in, the inner part of the neck orthosis at manufacture and the foam padding 1100 can be easily slotted in to, or removed from, the pocket as required.

In another embodiment, the padding element can be made by laminating different materials together to achieve the above describe behaviour. For example, a foam based substrate can have a fabric face bonded to it to wick moisture away from the skin surface. A suitable material that could be used in this approach would be Coolmax OB2048.

A wide number of variations are modifications to the specific embodiments of the invention described are possible and will be apparent to the skilled person in view of the description of the invention provided herein. For example, different materials can be used. Also, different specific sizes and/or shapes can be used depending on the intended patient and/or medical condition.

The invention claimed is:

1. A head support system for supporting a head of a patient having a medical condition, comprising:
    a neck orthosis formed from a flexible material, the flexible material being resiliently deformable and having an outer surface;
    a plurality of support members, each support member having a different form configured to provide a different type of support;
    a releasable attachment mechanism having a first part provided at the outer surface of, the neck orthosis and a second part provided at the support members such that the support members can be releasably attached to the outer surface of the neck orthosis to provide of support for the head;
    wherein the first part of the releasable attachment mechanism extends substantially over an entirety and/or continuously at the outer surface of the neck orthosis to allow each of the support members to be releasably attached to the neck orthosis to allow each of the support members to be releasably attached to the neck orthosis at a plurality of continuous positions; and
    wherein the support members comprise a core material and a covering, where the core material is resiliently deformable and is more rigid than the material of the neck orthosis, and the covering includes the second part of the releasable attachment mechanism.

2. The head support system of claim 1, wherein the first part of the releasable attachment mechanism extends over a first side, a second side, and a front and at least a part of a rear of the neck orthosis.

3. The head support system of claim 1, wherein the support members includes a first type of support member which has a flat elongate shape.

4. The head support system of claim 1, wherein the support members includes a second type of support member which is shaped to provide lateral support.

5. The head support system of claim 4, wherein the second type of support member is curved along a longitudinal axis and is also curved along a transverse axis.

6. The head support system of claim 1, wherein the support members includes a third type of support member which is shaped to provide support in a superior direction.

7. The head support system of claim 6, wherein the third type of support member is a lower jaw support.

8. The head support system of claim 6, wherein the third type of support member is shaped to provide support in a posterior direction also.

9. The head support system of claim 6, wherein the third type of support member has a zig-zag shape.

10. The head support system of claim 9, wherein the third type of support member has a central member, an upper member and a lower member and wherein the upper member is curved to accommodate a lower jaw of a patient in use and the lower member is shaped to accommodate an upper chest of a patient in use and wherein the central member is twisted in use.

11. The head support system of claim 1, wherein the support members includes a fourth type of support member configured to resiliently bias the neck orthosis in a posterior direction.

12. The head support system of claim 11, wherein the fourth type of support member is or includes a leaf spring.

13. The head support system of claim 12, wherein the leaf spring can transition from a curved state to a more linear state as the load applied to it increases.

14. The head support system of claim 11, wherein the fourth type of support member has a central member arranged to provide the resilient biasing, an upper member shaped to accommodate the rear of a patient's neck in use and a lower member shaped to accommodate an upper part of a patient's back in use.

15. The head support system of claim 11, wherein the fourth type of support member is generally J shaped.

16. The head support system of claim 1, wherein the support members includes a fifth type of support member which is shaped to support a chin.

17. The head support system of claim 16, wherein the fifth type of support member includes first and second side members and a first upper cross member extending between respective first ends of the first and second side members and a second lower cross member extending between the first and second side members.

18. The head support system of claim 1, wherein the neck orthosis further comprises:
    padding on or providing an inner surface of the neck orthosis and positioned at a front of the neck orthosis and defining an aperture within the padding element.

19. The head support system as claimed in claim 18, wherein the padding includes a first arm extending from a first side, a second arm extending from a second side and a tail extending downwardly.

20. The head support system of claim 1 wherein the neck orthosis comprises:
    a body made of a four-way stretch material which is flexible, the body having an outer surface, an inner surface, a top edge and a bottom edge; and
    a releasable fastener, wherein the top edge and bottom edge are shaped to cause the neck orthosis snuggly to conform to the anatomy of the patient adjacent the neck of the patient when the neck support is secured in use about the neck of the patient by the releasable fastener to support the head of the patient.

21. The head support system of claim 20, wherein the top edge comprises:
    a front portion shaped to receive an underside of a human lower jaw;
    a first side portion and a second side portion, each shaped to follow the mandible of a human; and
    a rear portion shaped to follow the lower cranium of a human.

22. The head support system of claim 20, wherein the bottom edge comprises:
    a front portion shaped to project inferiorly over the clavicle toward the upper sternal region;
    a first side portion and a second side portion, each shaped to project laterally and across the trapezius of a human; and
    a rear portion shaped to project inferiorly and over the cervical vertebrae a human.

23. The head support system of claim 20, wherein the body is constructed from a plurality of panels and wherein adjacent pairs of panels are joined by flat seams.

24. The head support system of claim 20, wherein each flat seam is formed by panel edges butting together and stitching.

25. The head support system of claim 20, wherein each flat seam is formed by bonding panel edges.

26. The head support system of claim 20 wherein the body is constructed from at least eight panels.

27. The head support system of claim 20, wherein the eight panels comprise a pair of front panels, a pair of forward side panels, a pair of rearward side panels and a pair of rear panels, and wherein the shape of each panel of the pair of panels is the same.

28. The head support system of claim 1, wherein the support member comprise hooks.

29. The head support system of claim 28, wherein the hooks are provided at a first side of the support members and a loop material is provide at a second side of the support members.

* * * * *